(12) United States Patent
Jump et al.

(10) Patent No.: US 11,674,127 B2
(45) Date of Patent: *Jun. 13, 2023

(54) PROCESS OF EXTRACTING OIL FROM THIN STILLAGE

(71) Applicant: NOVOZYMES A/S, Bagsvaerd (DK)

(72) Inventors: Joseph Jump, Raleigh, NC (US); Nathaniel Edward Kreel, Louisburg, NC (US); Bernardo Vidal, Jr., Wake Forest, NC (US); Chee-Leong Soong, Raleigh, NC (US); Madison Roberts, Raleigh, NC (US); Melissa Carrie Hooss, Franklinton, NC (US); Xinyu Shen, Wake Forest, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 213 days.

This patent is subject to a terminal disclaimer.

(21) Appl. No.: 17/306,001

(22) Filed: May 3, 2021

(65) Prior Publication Data

US 2021/0269781 A1    Sep. 2, 2021

Related U.S. Application Data

(63) Continuation of application No. 16/787,203, filed on Feb. 11, 2020, now Pat. No. 11,028,378, which is a continuation of application No. 16/062,519, filed as application No. PCT/US2016/067080 on Dec. 16, 2016, now Pat. No. 10,597,645.

(60) Provisional application No. 62/430,695, filed on Dec. 6, 2016, provisional application No. 62/324,107, filed on Apr. 18, 2016, provisional application No. 62/271,063, filed on Dec. 22, 2015, provisional application No. 62/271,182, filed on Dec. 22, 2015.

(51) Int. Cl.

| | |
|---|---|
| *C12N 9/14* | (2006.01) |
| *C12N 9/16* | (2006.01) |
| *C12N 9/20* | (2006.01) |
| *C12N 9/26* | (2006.01) |
| *C12N 9/28* | (2006.01) |
| *C12N 9/34* | (2006.01) |
| *C12N 9/42* | (2006.01) |
| *C12N 9/44* | (2006.01) |
| *C12N 9/50* | (2006.01) |
| *C12P 7/06* | (2006.01) |
| *C12P 19/14* | (2006.01) |
| *C12P 7/64* | (2022.01) |

(52) U.S. Cl.
CPC ............ *C12N 9/14* (2013.01); *C12N 9/16* (2013.01); *C12N 9/20* (2013.01); *C12N 9/2414* (2013.01); *C12N 9/2417* (2013.01); *C12N 9/2428* (2013.01); *C12N 9/2437* (2013.01); *C12N 9/2457* (2013.01); *C12N 9/50* (2013.01); *C12P 7/06* (2013.01); *C12P 19/14* (2013.01); *C12Y 301/03008* (2013.01); *C12Y 301/04* (2013.01); *C12Y 301/04011* (2013.01); *C12Y 302/01001* (2013.01); *C12Y 302/01003* (2013.01); *C12Y 302/01004* (2013.01); *C12Y 302/01008* (2013.01); *C12Y 302/01041* (2013.01); *C12Y 304/21062* (2013.01); *C12Y 304/23023* (2013.01); *C12Y 304/24039* (2013.01); *C12P 7/64* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 8,008,517 B2 | 8/2011 | Cantrell et al. | |
| 8,535,927 B1* | 9/2013 | Jones .................. | C11D 3/386 435/212 |
| 9,279,110 B2 | 3/2016 | Tang et al. | |
| 9,528,128 B2* | 12/2016 | Hansen ................ | C12P 7/06 |
| 9,816,112 B2 | 11/2017 | Deinhammer | |
| 10,597,645 B2 | 3/2020 | Jump et al. | |
| 11,028,378 B2 | 6/2021 | Jump et al. | |

FOREIGN PATENT DOCUMENTS

| | | |
|---|---|---|
| EP | 1905821 A1 | 4/2008 |
| WO | 2005/079193 A2 | 11/2005 |
| WO | 2011/126897 A2 | 10/2011 |

(Continued)

OTHER PUBLICATIONS

Devos et al, Proteins, Structures, Function and Genetics, vol. 41, pp. 98-107.

(Continued)

*Primary Examiner* — Suzanne M Noakes
*Assistant Examiner* — Jae W Lee
(74) *Attorney, Agent, or Firm* — David Fazzolare

(57) ABSTRACT

A process of recovering oil, comprising (a) converting a starch-containing material into dextrins with an alpha-amylase; (b) saccharifying the dextrins using a carbohydrate source generating enzyme to form a sugar; (c) fermenting the sugar in a fermentation medium into a fermentation product using a fermenting organism; (d) recovering the fermentation product to form a whole stillage; (e) separating the whole stillage into thin stillage and wet cake; (e') optionally concentrating the thin stillage into syrup; (f) recovering oil from the thin stillage and/or optionally the syrup, wherein a protease and a phospholipase are present and/or added during steps (a) to (c). Use of a protease and a phospholipase for increasing oil recovery yields from thin stillage and/or syrup in a fermentation product production process.

43 Claims, 1 Drawing Sheet
Specification includes a Sequence Listing.

(56) References Cited

FOREIGN PATENT DOCUMENTS

| WO | 2014/074452 A1 | 5/2014 |
|---|---|---|
| WO | 2014/090161 A1 | 6/2014 |
| WO | 2014/209789 A1 | 12/2014 |
| WO | 2015/116395 A1 | 8/2015 |
| WO | 2015/173426 A1 | 11/2015 |
| WO | 2015173426 A1 | 11/2015 |

OTHER PUBLICATIONS

Majoni et al, 2010, J Am Oil Chem Soc 88(4), 523-532.
Wang et al, 2009, J Agric Food Chem 57(6), 2302-2307.

* cited by examiner

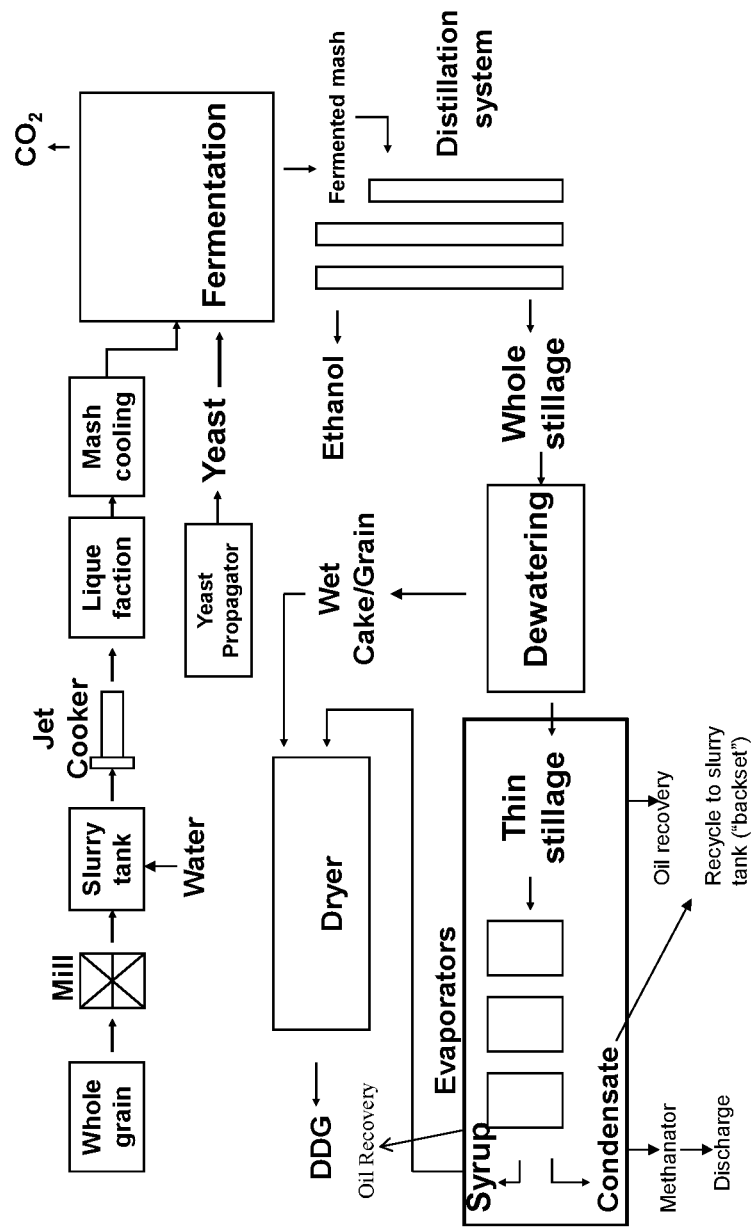

SEQUENCE LISTING

<160> NUMBER OF SEQ ID NOS: 17

<210> SEQ ID NO 1
<211> LENGTH: 515
<212> TYPE: PRT
<213> ORGANISM: Bacillus stearothermophilus
<220> FEATURE:
<221> NAME/KEY: mat_peptide
<222> LOCATION: (1)..(515)

<400> SEQUENCE: 1

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

```
Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 2
<211> LENGTH: 1068
<212> TYPE: DNA
<213> ORGANISM: Thermoascus aurantiacus
<220> FEATURE:
<221> NAME/KEY: CDS
<222> LOCATION: (1)..(1065)
<220> FEATURE:
<221> NAME/KEY: misc_signal
<222> LOCATION: (1)..(57)
<220> FEATURE:
<221> NAME/KEY: misc_feature
<222> LOCATION: (58)..(534)
<220> FEATURE:
<221> NAME/KEY: mat_peptide
<222> LOCATION: (535)..(1068)

<400> SEQUENCE: 2 atg cgg ctc gtt gct tcc cta acg gcc ttg gtg gcc ttg tcc gta          45
Met Arg Leu Val Ala Ser Leu Thr Ala Leu Val Ala Leu Ser Val
        -175                -170                -165 cct gtc ttt ccc gct gct gtc aac gtg aag cgt gct tcg tcc tac          90
Pro Val Phe Pro Ala Ala Val Asn Val Lys Arg Ala Ser Ser Tyr
        -160                -155                -150 ctg gag atc act ctg agc cag gtc agc aac act ctg atc aag gcc         135
Leu Glu Ile Thr Leu Ser Gln Val Ser Asn Thr Leu Ile Lys Ala
        -145                -140                -135 gtg gtc cag aac act ggt agc gac gag ttg tcc ttc gtt cac ctg         180
Val Val Gln Asn Thr Gly Ser Asp Glu Leu Ser Phe Val His Leu
        -130                -125                -120 aac ttc ttc aag gac ccc gct cct gtc aaa aag gta tcg gtc tat         225
Asn Phe Phe Lys Asp Pro Ala Pro Val Lys Lys Val Ser Val Tyr
        -115                -110                -105 cgc gat ggg tct gaa gtg cag ttc gag ggc att ttg agc cgc tac aaa     273
Arg Asp Gly Ser Glu Val Gln Phe Glu Gly Ile Leu Ser Arg Tyr Lys
        -100                 -95                 -90 tcg act ggc ctc tct cgt gac gcc ttt act tat ctg gct ccc gga gag    321
Ser Thr Gly Leu Ser Arg Asp Ala Phe Thr Tyr Leu Ala Pro Gly Glu
```

-continued

```
            -85                 -80                 -75
tcc gtc gag gac gtt ttt gat att gct tcg act tac gat ctg acc agc      369
Ser Val Glu Asp Val Phe Asp Ile Ala Ser Thr Tyr Asp Leu Thr Ser
    -70                 -65                 -60 ggc ggc cct gta act atc cgt act gag gga gtt gtt ccc tac gcc acg      417
Gly Gly Pro Val Thr Ile Arg Thr Glu Gly Val Val Pro Tyr Ala Thr
-55                 -50                 -45                 -40 gct aac agc act gat att gcc ggc tac atc tca tac tcg tct aat gtg      465
Ala Asn Ser Thr Asp Ile Ala Gly Tyr Ile Ser Tyr Ser Ser Asn Val
            -35                 -30                 -25 ttg acc att gat gtc gat ggc gcc gct gct gcc act gtc tcc aag gca      513
Leu Thr Ile Asp Val Asp Gly Ala Ala Ala Ala Thr Val Ser Lys Ala
        -20                 -15                 -10 atc act cct ttg gac cgc cgc act agg atc agt tcc tgc tcc ggc agc      561
Ile Thr Pro Leu Asp Arg Arg Thr Arg Ile Ser Ser Cys Ser Gly Ser
    -5                  -1  1                 5 aga cag agc gct ctt act acg gct ctc aga aac gct gct tct ctt gcc      609
Arg Gln Ser Ala Leu Thr Thr Ala Leu Arg Asn Ala Ala Ser Leu Ala
10                  15                  20                  25 aac gca gct gcc gac gcg gct cag tct gga tca gct tca aag ttc agc      657
Asn Ala Ala Ala Asp Ala Ala Gln Ser Gly Ser Ala Ser Lys Phe Ser
                30                  35                  40 gag tac ttc aag act act tct agc tct acc cgc cag acc gtg gct gcg      705
Glu Tyr Phe Lys Thr Thr Ser Ser Ser Thr Arg Gln Thr Val Ala Ala
            45                  50                  55 cgt ctt cgg gct gtt gcg cgg gag gca tct tcg tct tct tcg gga gcc      753
Arg Leu Arg Ala Val Ala Arg Glu Ala Ser Ser Ser Ser Ser Gly Ala
        60                  65                  70 acc acg tac tac tgc gac gat ccc tac ggc tac tgt tcc tcc aac gtc      801
Thr Thr Tyr Tyr Cys Asp Asp Pro Tyr Gly Tyr Cys Ser Ser Asn Val
    75                  80                  85 ctg gct tac acc ctg cct tca tac aac ata atc gcc aac tgt gac att      849
Leu Ala Tyr Thr Leu Pro Ser Tyr Asn Ile Ile Ala Asn Cys Asp Ile
90                  95                  100                 105 ttc tat act tac ctg ccg gct ctg acc agt acc tgt cac gct cag gat      897
Phe Tyr Thr Tyr Leu Pro Ala Leu Thr Ser Thr Cys His Ala Gln Asp
                110                 115                 120 caa gcg acc act gcc ctt cac gag ttc acc cat gcg cct ggc gtc tac      945
Gln Ala Thr Thr Ala Leu His Glu Phe Thr His Ala Pro Gly Val Tyr
            125                 130                 135 agc cct ggc acg gac gac ctg gcg tat ggc tac cag gct gcg atg ggt      993
Ser Pro Gly Thr Asp Asp Leu Ala Tyr Gly Tyr Gln Ala Ala Met Gly
        140                 145                 150 ctc agc agc agc cag gct gtc atg aac gct gac acc tac gct ctc tat      1041
Leu Ser Ser Ser Gln Ala Val Met Asn Ala Asp Thr Tyr Ala Leu Tyr
    155                 160                 165 gcg aat gcc ata tac ctt ggt tgc taa                                  1068
Ala Asn Ala Ile Tyr Leu Gly Cys
170                 175

<210> SEQ ID NO 3
<211> LENGTH: 355
<212> TYPE: PRT
<213> ORGANISM: Thermoascus aurantiacus

<400> SEQUENCE: 3

Met Arg Leu Val   Ala Ser Leu Thr   Ala Leu Val Ala   Leu Ser   Val
            -175                -170                -165

Pro Val Phe Pro   Ala Ala Val Asn   Val Lys Arg Ala   Ser Ser   Tyr
            -160                -155                -150
```

Leu Glu Ile Thr Leu Ser Gln Val Ser Asn Thr Leu Ile Lys Ala
         -145              -140              -135

Val Val Gln Asn Thr Gly Ser Asp Glu Leu Ser Phe Val His Leu
        -130              -125              -120

Asn Phe Phe Lys Asp Pro Ala Pro Val Lys Lys Val Ser Val Tyr
        -115              -110              -105

Arg Asp Gly Ser Glu Val Gln Phe Glu Gly Ile Leu Ser Arg Tyr Lys
        -100               -95                   -90

Ser Thr Gly Leu Ser Arg Asp Ala Phe Thr Tyr Leu Ala Pro Gly Glu
         -85              -80                -75

Ser Val Glu Asp Val Phe Asp Ile Ala Ser Thr Tyr Asp Leu Thr Ser
     -70              -65                -60

Gly Gly Pro Val Thr Ile Arg Thr Glu Gly Val Val Pro Tyr Ala Thr
-55              -50              -45                   -40

Ala Asn Ser Thr Asp Ile Ala Gly Tyr Ile Ser Tyr Ser Ser Asn Val
             -35              -30                   -25

Leu Thr Ile Asp Val Asp Gly Ala Ala Ala Thr Val Ser Lys Ala
         -20              -15                -10

Ile Thr Pro Leu Asp Arg Arg Thr Arg Ile Ser Ser Cys Ser Gly Ser
         -5            -1   1                   5

Arg Gln Ser Ala Leu Thr Thr Ala Leu Arg Asn Ala Ala Ser Leu Ala
10                  15                  20                  25

Asn Ala Ala Ala Asp Ala Ala Gln Ser Gly Ser Ala Ser Lys Phe Ser
                30                  35                  40

Glu Tyr Phe Lys Thr Thr Ser Ser Thr Arg Gln Thr Val Ala Ala
                45                  50                  55

Arg Leu Arg Ala Val Ala Arg Glu Ala Ser Ser Ser Ser Gly Ala
60                  65                      70

Thr Thr Tyr Tyr Cys Asp Asp Pro Tyr Gly Tyr Cys Ser Ser Asn Val
         75                  80                  85

Leu Ala Tyr Thr Leu Pro Ser Tyr Asn Ile Ile Ala Asn Cys Asp Ile
90                  95                  100                 105

Phe Tyr Thr Tyr Leu Pro Ala Leu Thr Ser Thr Cys His Ala Gln Asp
                110                 115                 120

Gln Ala Thr Thr Ala Leu His Glu Phe Thr His Ala Pro Gly Val Tyr
                125                 130                 135

Ser Pro Gly Thr Asp Asp Leu Ala Tyr Gly Tyr Gln Ala Ala Met Gly
        140                 145                 150

Leu Ser Ser Ser Gln Ala Val Met Asn Ala Asp Thr Tyr Ala Leu Tyr
        155                 160                 165

Ala Asn Ala Ile Tyr Leu Gly Cys
170                 175

<210> SEQ ID NO 4
<211> LENGTH: 412
<212> TYPE: PRT
<213> ORGANISM: Pyrococcus furiosus
<220> FEATURE:
<221> NAME/KEY: mat_peptide
<222> LOCATION: (1)..(412)
<223> OTHER INFORMATION: Pyrococcus furiosus protease (Pfu)

<400> SEQUENCE: 4

Ala Glu Leu Glu Gly Leu Asp Glu Ser Ala Ala Gln Val Met Ala Thr
1               5                   10                  15

```
Tyr Val Trp Asn Leu Gly Tyr Asp Ser Gly Ile Thr Ile Gly Ile
             20              25              30
Ile Asp Thr Gly Ile Asp Ala Ser His Pro Asp Leu Gln Gly Lys Val
         35              40                  45
Ile Gly Trp Val Asp Phe Val Asn Gly Arg Ser Tyr Pro Tyr Asp Asp
     50              55                  60
His Gly His Gly Thr His Val Ala Ser Ile Ala Ala Gly Thr Gly Ala
65              70                  75              80
Ala Ser Asn Gly Lys Tyr Lys Gly Met Ala Pro Gly Ala Lys Leu Ala
             85                  90                  95
Gly Ile Lys Val Leu Gly Ala Asp Gly Ser Gly Ser Ile Ser Thr Ile
         100             105                 110
Ile Lys Gly Val Glu Trp Ala Val Asp Asn Lys Asp Lys Tyr Gly Ile
     115             120                 125
Lys Val Ile Asn Leu Ser Leu Gly Ser Ser Gln Ser Ser Asp Gly Thr
130             135                 140
Asp Ala Leu Ser Gln Ala Val Asn Ala Ala Trp Asp Ala Gly Leu Val
145             150                 155                 160
Val Val Val Ala Ala Gly Asn Ser Gly Pro Asn Lys Tyr Thr Ile Gly
             165             170                 175
Ser Pro Ala Ala Ala Ser Lys Val Ile Thr Val Gly Ala Val Asp Lys
         180             185                 190
Tyr Asp Val Ile Thr Ser Phe Ser Ser Arg Gly Pro Thr Ala Asp Gly
     195             200                 205
Arg Leu Lys Pro Glu Val Val Ala Pro Gly Asn Trp Ile Ile Ala Ala
210             215                 220
Arg Ala Ser Gly Thr Ser Met Gly Gln Pro Ile Asn Asp Tyr Tyr Thr
225             230                 235                 240
Ala Ala Pro Gly Thr Ser Met Ala Thr Pro His Val Ala Gly Ile Ala
             245             250                 255
Ala Leu Leu Leu Gln Ala His Pro Ser Trp Thr Pro Asp Lys Val Lys
         260             265                 270
Thr Ala Leu Ile Glu Thr Ala Asp Ile Val Lys Pro Asp Glu Ile Ala
     275             280                 285
Asp Ile Ala Tyr Gly Ala Gly Arg Val Asn Ala Tyr Lys Ala Ile Asn
290             295                 300
Tyr Asp Asn Tyr Ala Lys Leu Val Phe Thr Gly Tyr Val Ala Asn Lys
305             310                 315                 320
Gly Ser Gln Thr His Gln Phe Val Ile Ser Gly Ala Ser Phe Val Thr
             325             330                 335
Ala Thr Leu Tyr Trp Asp Asn Ala Asn Ser Asp Leu Asp Leu Tyr Leu
         340             345                 350
Tyr Asp Pro Asn Gly Asn Gln Val Asp Tyr Ser Tyr Thr Ala Tyr Tyr
     355             360                 365
Gly Phe Glu Lys Val Gly Tyr Tyr Asn Pro Thr Asp Gly Thr Trp Thr
     370             375                 380
Ile Lys Val Val Ser Tyr Ser Gly Ser Ala Asn Tyr Gln Val Asp Val
385             390                 395                 400
Val Ser Asp Gly Ser Leu Ser Gln Pro Gly Ser Ser
             405             410

<210> SEQ ID NO 5
<211> LENGTH: 49
<212> TYPE: DNA
```

-continued

<213> ORGANISM: Artificial Sequence
<220> FEATURE:
<223> OTHER INFORMATION: Primer

<400> SEQUENCE: 5
aacgacggta cccgggatc ggatccatgc ggctcgttgc ttccctaac            49

<210> SEQ ID NO 6
<211> LENGTH: 48
<212> TYPE: DNA
<213> ORGANISM: Artificial Sequence
<220> FEATURE:
<223> OTHER INFORMATION: Primer

<400> SEQUENCE: 6
ctaattacat gatgcggccc ttaattaatt agcaaccaag gtatatgg            48

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
taggagttta gtgaacttgc                                           20

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
ttcgagcgtc ccaaaacc                                             18

<210> SEQ ID NO 9
<211> LENGTH: 430
<212> TYPE: PRT
<213> ORGANISM: Rhizomucor miehei
<220> FEATURE:
<221> NAME/KEY: SIGNAL
<222> LOCATION: (1)..(22)
<220> FEATURE:
<221> NAME/KEY: mat_peptide
<222> LOCATION: (33)..(430)

<400> SEQUENCE: 9

Met Leu Phe Ser Gln Ile Thr Ser Ala Ile Leu Leu Thr Ala Ala Ser
        -30                 -25                 -20

Leu Ser Leu Thr Thr Ala Arg Pro Val Ser Lys Gln Ser Glu Ser Lys
    -15                 -10                  -5                  -1

Asp Lys Leu Leu Ala Leu Pro Leu Thr Ser Val Ser Arg Lys Phe Ser
1                5                  10                  15

Gln Thr Lys Phe Gly Gln Gln Gln Leu Ala Glu Lys Leu Ala Gly Leu
            20                  25                  30

Lys Pro Phe Ser Glu Ala Ala Ala Asp Gly Ser Val Asp Thr Pro Gly
        35                  40                  45

Tyr Tyr Asp Phe Asp Leu Glu Glu Tyr Ala Ile Pro Val Ser Ile Gly
    50                  55                  60

Thr Pro Gly Gln Asp Phe Leu Leu Leu Phe Asp Thr Gly Ser Ser Asp
65                  70                  75                  80

```
Thr Trp Val Pro His Lys Gly Cys Thr Lys Ser Glu Gly Cys Val Gly
                85                  90                  95

Ser Arg Phe Phe Asp Pro Ser Ala Ser Ser Thr Phe Lys Ala Thr Asn
            100                 105                 110

Tyr Asn Leu Asn Ile Thr Tyr Gly Thr Gly Gly Ala Asn Gly Leu Tyr
        115                 120                 125

Phe Glu Asp Ser Ile Ala Ile Gly Asp Ile Thr Val Thr Lys Gln Ile
    130                 135                 140

Leu Ala Tyr Val Asp Asn Val Arg Gly Pro Thr Ala Glu Gln Ser Pro
145                 150                 155                 160

Asn Ala Asp Ile Phe Leu Asp Gly Leu Phe Gly Ala Ala Tyr Pro Asp
                165                 170                 175

Asn Thr Ala Met Glu Ala Glu Tyr Gly Ser Thr Tyr Asn Thr Val His
            180                 185                 190

Val Asn Leu Tyr Lys Gln Gly Leu Ile Ser Ser Pro Leu Phe Ser Val
        195                 200                 205

Tyr Met Asn Thr Asn Ser Gly Thr Gly Glu Val Phe Gly Gly Val
    210                 215                 220

Asn Asn Thr Leu Leu Gly Gly Asp Ile Ala Tyr Thr Asp Val Met Ser
225                 230                 235                 240

Arg Tyr Gly Gly Tyr Tyr Phe Trp Asp Ala Pro Val Thr Gly Ile Thr
                245                 250                 255

Val Asp Gly Ser Ala Ala Val Arg Phe Ser Arg Pro Gln Ala Phe Thr
            260                 265                 270

Ile Asp Thr Gly Thr Asn Phe Phe Ile Met Pro Ser Ser Ala Ala Ser
        275                 280                 285

Lys Ile Val Lys Ala Ala Leu Pro Asp Ala Thr Glu Thr Gln Gln Gly
290                 295                 300

Trp Val Val Pro Cys Ala Ser Tyr Gln Asn Ser Lys Ser Thr Ile Ser
305                 310                 315                 320

Ile Val Met Gln Lys Ser Gly Ser Ser Ser Asp Thr Ile Glu Ile Ser
                325                 330                 335

Val Pro Val Ser Lys Met Leu Leu Pro Val Asp Gln Ser Asn Glu Thr
            340                 345                 350

Cys Met Phe Ile Ile Leu Pro Asp Gly Gly Asn Gln Tyr Ile Val Gly
        355                 360                 365

Asn Leu Phe Leu Arg Phe Phe Val Asn Val Tyr Asp Phe Gly Asn Asn
370                 375                 380

Arg Ile Gly Phe Ala Pro Leu Ala Ser Ala Tyr Glu Asn Glu
385                 390                 395

<210> SEQ ID NO 10
<211> LENGTH: 368
<212> TYPE: PRT
<213> ORGANISM: Thermobifida fusca
<220> FEATURE:
<221> NAME/KEY: SIGNAL
<222> LOCATION: (1)..(32)
<220> FEATURE:
<221> NAME/KEY: mat_peptide
<222> LOCATION: (33)..(368)

<400> SEQUENCE: 10

Met Asn His Ser Ser Arg Arg Thr Thr Ser Leu Leu Phe Thr Ala Ala
        -30                 -25                 -20

Leu Ala Ala Thr Ala Leu Val Ala Ala Thr Thr Pro Ala Ser Ala Gln
        -15                 -10                 -5                  -1
```

Glu Leu Ala Leu Lys Arg Asp Leu Gly Leu Ser Asp Ala Glu Val Ala
1               5                   10                  15

Glu Leu Arg Ala Ala Glu Ala Glu Val Glu Leu Glu Glu Glu Leu
            20                  25                  30

Arg Asp Ser Leu Gly Ser Asp Phe Gly Gly Val Tyr Leu Asp Ala Asp
            35                  40                  45

Thr Thr Glu Ile Thr Val Ala Val Thr Asp Pro Ala Ala Val Ser Arg
50                  55                  60

Val Asp Ala Asp Asp Val Thr Val Asp Val Val Asp Phe Gly Glu Thr
65                  70                  75                  80

Ala Leu Asn Asp Phe Val Ala Ser Leu Asn Ala Ile Ala Asp Thr Ala
                85                  90                  95

Asp Pro Lys Val Thr Gly Trp Tyr Thr Asp Leu Glu Ser Asp Ala Val
            100                 105                 110

Val Ile Thr Thr Leu Arg Gly Gly Thr Pro Ala Ala Glu Glu Leu Ala
            115                 120                 125

Glu Arg Ala Gly Leu Asp Glu Arg Ala Val Arg Ile Val Glu Glu Asp
            130                 135                 140

Glu Glu Pro Gln Ser Leu Ala Ala Ile Ile Gly Gly Asn Pro Tyr Tyr
145                 150                 155                 160

Phe Gly Asn Tyr Arg Cys Ser Ile Gly Phe Ser Val Arg Gln Gly Ser
                165                 170                 175

Gln Thr Gly Phe Ala Thr Ala Gly His Cys Gly Ser Thr Gly Thr Arg
            180                 185                 190

Val Ser Ser Pro Ser Gly Thr Val Ala Gly Ser Tyr Phe Pro Gly Arg
            195                 200                 205

Asp Met Gly Trp Val Arg Ile Thr Ser Ala Asp Thr Val Thr Pro Leu
210                 215                 220

Val Asn Arg Tyr Asn Gly Gly Thr Val Thr Val Thr Gly Ser Gln Glu
225                 230                 235                 240

Ala Ala Thr Gly Ser Ser Val Cys Arg Ser Gly Ala Thr Thr Gly Trp
                245                 250                 255

Arg Cys Gly Thr Ile Gln Ser Lys Asn Gln Thr Val Arg Tyr Ala Glu
            260                 265                 270

Gly Thr Val Thr Gly Leu Thr Arg Thr Thr Ala Cys Ala Glu Gly Gly
            275                 280                 285

Asp Ser Gly Gly Pro Trp Leu Thr Gly Ser Gln Ala Gln Gly Val Thr
            290                 295                 300

Ser Gly Gly Thr Gly Asp Cys Arg Ser Gly Gly Ile Thr Phe Phe Gln
305                 310                 315                 320

Pro Ile Asn Pro Leu Leu Ser Tyr Phe Gly Leu Gln Leu Val Thr Gly
                325                 330                 335

<210> SEQ ID NO 11
<211> LENGTH: 583
<212> TYPE: PRT
<213> ORGANISM: Artificial Sequence
<220> FEATURE:
<223> OTHER INFORMATION: Hybrid protein sequence

<400> SEQUENCE: 11

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

-continued

```
Ser Asn Tyr Cys Gly Gly Thr Tyr Glu Gly Ile Thr Lys His Leu Asp
         35                  40                  45

Tyr Ile Ser Gly Met Gly Phe Asp Ala Ile Trp Ile Ser Pro Ile Pro
     50                  55                  60

Lys Asn Ser Asp Gly Gly Tyr His Gly Tyr Trp Ala Thr Asp Phe Tyr
 65                  70                  75                  80

Gln Leu Asn Ser Asn Phe Gly Asp Glu Ser Gln Leu Lys Ala Leu Ile
                 85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
    290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
    370                 375                 380

Gly Ser Gly Ser Thr Asn Gln Val Ser Phe Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Ala Thr Pro
        435                 440                 445
```

```
Thr Gly Ser Gly Ser Val Thr Ser Thr Ser Lys Thr Thr Ala Thr Ala
        450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
        515                 520                 525

Leu Trp Tyr Val Thr Val Thr Leu Pro Ala Gly Glu Ser Phe Glu Tyr
530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 12
<211> LENGTH: 573
<212> TYPE: PRT
<213> ORGANISM: Gloeophyllum sepiarium
<220> FEATURE:
<221> NAME/KEY: SIGNAL
<222> LOCATION: (1)..(17)
<220> FEATURE:
<221> NAME/KEY: mat_peptide
<222> LOCATION: (18)..(573)

<400> SEQUENCE: 12

Met Tyr Arg Phe Leu Val Cys Ala Leu Gly Leu Ala Ala Ser Val Leu
            -15                 -10                  -5

Ala Gln Ser Val Asp Ser Tyr Val Ser Ser Glu Gly Pro Ile Ala Lys
 -1  1               5                  10                  15

Ala Gly Val Leu Ala Asn Ile Gly Pro Asn Gly Ser Lys Ala Ser Gly
                 20                  25                  30

Ala Ser Ala Gly Val Val Ala Ser Pro Ser Thr Ser Asp Pro Asp
             35                  40                  45

Tyr Trp Tyr Thr Trp Thr Arg Asp Ser Ser Leu Val Phe Lys Ser Leu
         50                  55                  60

Ile Asp Gln Tyr Thr Thr Gly Ile Asp Ser Thr Ser Ser Leu Arg Thr
 65                  70                  75

Leu Ile Asp Asp Phe Val Thr Ala Glu Ala Asn Leu Gln Gln Val Ser
 80                  85                  90                  95

Asn Pro Ser Gly Thr Leu Thr Thr Gly Gly Leu Gly Glu Pro Lys Phe
                100                 105                 110

Asn Val Asp Glu Thr Ala Phe Thr Gly Ala Trp Gly Arg Pro Gln Arg
                115                 120                 125

Asp Gly Pro Ala Leu Arg Ser Thr Ala Leu Ile Thr Tyr Gly Asn Trp
            130                 135                 140

Leu Leu Ser Asn Gly Asn Thr Ser Tyr Val Thr Ser Asn Leu Trp Pro
145                 150                 155

Ile Ile Gln Asn Asp Leu Gly Tyr Val Val Ser Tyr Trp Asn Gln Ser
160                 165                 170                 175

Thr Tyr Asp Leu Trp Glu Glu Val Asp Ser Ser Phe Phe Thr Thr
                180                 185                 190
```

Ala Val Gln His Arg Ala Leu Arg Glu Gly Ala Ala Phe Ala Thr Ala
            195                 200                 205

Ile Gly Gln Thr Ser Gln Val Ser Ser Tyr Thr Thr Gln Ala Asp Asn
210                 215                 220

Leu Leu Cys Phe Leu Gln Ser Tyr Trp Asn Pro Ser Gly Gly Tyr Ile
        225                 230                 235

Thr Ala Asn Thr Gly Gly Arg Ser Gly Lys Asp Ala Asn Thr Leu
240                 245                 250                 255

Leu Ala Ser Ile His Thr Tyr Asp Pro Ser Ala Gly Cys Asp Ala Ala
            260                 265                 270

Thr Phe Gln Pro Cys Ser Asp Lys Ala Leu Ser Asn Leu Lys Val Tyr
        275                 280                 285

Val Asp Ser Phe Arg Ser Val Tyr Ser Ile Asn Ser Gly Val Ala Ser
        290                 295                 300

Asn Ala Ala Val Ala Thr Gly Arg Tyr Pro Glu Asp Ser Tyr Gln Gly
305                 310                 315

Gly Asn Pro Trp Tyr Leu Thr Thr Phe Ala Val Ala Glu Gln Leu Tyr
320                 325                 330                 335

Asp Ala Leu Asn Val Trp Glu Ser Gln Gly Ser Leu Glu Val Thr Ser
            340                 345                 350

Thr Ser Leu Ala Phe Phe Gln Gln Phe Ser Ser Gly Val Thr Ala Gly
        355                 360                 365

Thr Tyr Ser Ser Ser Ser Ser Thr Tyr Ser Thr Leu Thr Ser Ala Ile
        370                 375                 380

Lys Asn Phe Ala Asp Gly Phe Val Ala Ile Asn Ala Lys Tyr Thr Pro
385                 390                 395

Ser Asn Gly Gly Leu Ala Glu Gln Tyr Ser Lys Ser Asp Gly Ser Pro
400                 405                 410                 415

Leu Ser Ala Val Asp Leu Thr Trp Ser Tyr Ala Ser Ala Leu Thr Ala
            420                 425                 430

Phe Glu Ala Arg Asn Asn Thr Gln Phe Ala Gly Trp Gly Ala Ala Gly
        435                 440                 445

Leu Thr Val Pro Ser Ser Cys Ser Gly Asn Ser Gly Pro Thr Val
        450                 455                 460

Ala Val Thr Phe Asn Val Asn Ala Glu Thr Val Trp Gly Glu Asn Ile
465                 470                 475

Tyr Leu Thr Gly Ser Val Asp Ala Leu Glu Asn Trp Ser Ala Asp Asn
480                 485                 490                 495

Ala Leu Leu Leu Ser Ser Ala Asn Tyr Pro Thr Trp Ser Ile Thr Val
            500                 505                 510

Asn Leu Pro Ala Ser Thr Ala Ile Glu Tyr Lys Tyr Ile Arg Lys Asn
        515                 520                 525

Asn Gly Ala Val Thr Trp Glu Ser Asp Pro Asn Asn Ser Ile Thr Thr
        530                 535                 540

Pro Ala Ser Gly Ser Thr Thr Glu Asn Asp Thr Trp Arg
545                 550                 555

<210> SEQ ID NO 13
<211> LENGTH: 573
<212> TYPE: PRT
<213> ORGANISM: Pycnoporus sanguineus
<220> FEATURE:
<221> NAME/KEY: SIGNAL
<222> LOCATION: (1)..(18)
<220> FEATURE:

<221> NAME/KEY: mat_peptide
<222> LOCATION: (19)..(573)

<400> SEQUENCE: 13

Met Arg Phe Thr Leu Leu Ala Ser Leu Ile Gly Leu Ala Val Gly Ala
                -15                 -10                  -5

Phe Ala Gln Ser Ser Ala Val Asp Ala Tyr Val Ala Ser Glu Ser Pro
     -1   1                   5                  10

Ile Ala Lys Gln Gly Val Leu Asn Asn Ile Gly Pro Asn Gly Ser Lys
 15              20                  25                      30

Ala His Gly Ala Lys Ala Gly Ile Val Val Ala Ser Pro Ser Thr Glu
                 35                  40                  45

Asn Pro Asp Tyr Leu Tyr Thr Trp Thr Arg Asp Ser Ser Leu Val Phe
             50                  55                  60

Lys Leu Leu Ile Asp Gln Phe Thr Ser Gly Asp Asp Thr Ser Leu Arg
             65                  70                  75

Gly Leu Ile Asp Asp Phe Thr Ser Ala Glu Ala Ile Leu Gln Gln Val
         80                  85                  90

Ser Asn Pro Ser Gly Thr Val Ser Thr Gly Gly Leu Gly Glu Pro Lys
 95              100                 105                    110

Phe Asn Ile Asp Glu Thr Ala Phe Thr Gly Ala Trp Gly Arg Pro Gln
                 115                 120                    125

Arg Asp Gly Pro Ala Leu Arg Ala Thr Ser Ile Ile Arg Tyr Ala Asn
             130                 135                 140

Trp Leu Leu Asp Asn Gly Asn Thr Thr Tyr Val Ser Asn Thr Leu Trp
             145                 150                 155

Pro Val Ile Gln Leu Asp Leu Asp Tyr Val Ala Asp Asn Trp Asn Gln
         160                 165                 170

Ser Thr Phe Asp Leu Trp Glu Glu Val Asp Ser Ser Phe Phe Thr
 175                 180                 185                 190

Thr Ala Val Gln His Arg Ala Leu Arg Glu Gly Ala Thr Phe Ala Ser
                 195                 200                 205

Arg Ile Gly Gln Ser Ser Val Val Ser Gly Tyr Thr Thr Gln Ala Asp
             210                 215                 220

Asn Leu Leu Cys Phe Leu Gln Ser Tyr Trp Asn Pro Ser Gly Gly Tyr
             225                 230                 235

Val Thr Ala Asn Thr Gly Gly Arg Ser Gly Lys Asp Ser Asn Thr
         240                 245                 250

Val Leu Thr Ser Ile His Thr Phe Asp Pro Ala Ala Gly Cys Asp Ala
 255                 260                 265                 270

Ala Thr Phe Gln Pro Cys Ser Asp Lys Ala Leu Ser Asn Leu Lys Val
                 275                 280                 285

Tyr Val Asp Ala Phe Arg Ser Ile Tyr Thr Ile Asn Asn Gly Ile Ala
             290                 295                 300

Ser Asn Ala Ala Val Ala Thr Gly Arg Tyr Pro Glu Asp Ser Tyr Met
             305                 310                 315

Gly Gly Asn Pro Trp Tyr Leu Thr Thr Ser Ala Val Ala Glu Gln Leu
             320                 325                 330

Tyr Asp Ala Leu Tyr Val Trp Asp Gln Leu Gly Gly Leu Asn Val Thr
 335                 340                 345                 350

Ser Thr Ser Leu Ala Phe Phe Gln Gln Phe Ala Ser Gly Leu Ser Thr
                 355                 360                 365

Gly Thr Tyr Ser Ala Ser Ser Ser Thr Tyr Ala Thr Leu Thr Ser Ala
             370                 375                 380

```
Ile Arg Ser Phe Ala Asp Gly Phe Leu Ala Ile Asn Ala Lys Tyr Thr
        385                 390                 395

Pro Ala Asp Gly Gly Leu Ala Glu Gln Tyr Ser Arg Asn Asp Gly Thr
400                 405                 410

Pro Leu Ser Ala Val Asp Leu Thr Trp Ser Tyr Ala Ala Ala Leu Thr
415                 420                 425                 430

Ala Phe Ala Ala Arg Glu Gly Lys Thr Tyr Gly Ser Trp Gly Ala Ala
            435                 440                 445

Gly Leu Thr Val Pro Ala Ser Cys Ser Gly Gly Gly Ala Thr Val
                450                 455                 460

Ala Val Thr Phe Asn Val Gln Ala Thr Val Phe Gly Glu Asn Ile
            465                 470                 475

Tyr Ile Thr Gly Ser Val Ala Ala Leu Gln Asn Trp Ser Pro Asp Asn
        480                 485                 490

Ala Leu Ile Leu Ser Ala Ala Asn Tyr Pro Thr Trp Ser Ile Thr Val
495                 500                 505                 510

Asn Leu Pro Ala Asn Thr Val Val Gln Tyr Lys Tyr Ile Arg Lys Phe
                515                 520                 525

Asn Gly Gln Val Thr Trp Glu Ser Asp Pro Asn Gln Ile Thr Thr
            530                 535                 540

Pro Ser Gly Gly Ser Phe Thr Gln Asn Asp Val Trp Arg
    545                 550                 555
```

<210> SEQ ID NO 14
<211> LENGTH: 564
<212> TYPE: PRT
<213> ORGANISM: Meripilus giganteus
<220> FEATURE:
<221> NAME/KEY: SIGNAL
<222> LOCATION: (1)..(17)
<220> FEATURE:
<221> NAME/KEY: mat_peptide
<222> LOCATION: (18)..(564)

<400> SEQUENCE: 14

```
Met Val Ala Thr Ser Leu Leu Val Ala Ser Leu Phe Thr Leu Ala Leu
        -15                 -10                 -5

Gly Thr Pro Thr Gly Arg Asn Leu Lys Leu His Glu Ala Arg Glu Asp
-1  1                   5                   10                  15

Leu Pro Ala Gly Phe Ser Leu Arg Gly Ala Ala Ser Pro Asp Thr Thr
                20                  25                  30

Leu Lys Leu Arg Ile Ala Leu Val Gln Asn Asn Phe Ala Glu Leu Glu
            35                  40                  45

Asp Lys Leu Tyr Asp Val Ser Thr Pro Ser Ser Ala Asn Tyr Gly Asn
        50                  55                  60

His Leu Ser Lys Glu Glu Val Glu Gln Tyr Ile Ala Pro Ala Pro Glu
65                  70                  75

Ser Val Lys Ala Val Asn Ala Trp Leu Thr Glu Asn Gly Leu Asp Ala
80                  85                  90                  95

His Thr Ile Ser Pro Ala Gly Asp Trp Leu Ala Phe Glu Val Pro Val
                100                 105                 110

Ser Lys Ala Asn Glu Leu Phe Asp Ala Asp Phe Ser Val Phe Thr His
            115                 120                 125

Asp Glu Ser Gly Leu Glu Ala Ile Arg Thr Leu Ala Tyr Ser Ile Pro
        130                 135                 140

Ala Glu Leu Gln Gly His Leu Asp Leu Val His Pro Thr Val Thr Phe
```

```
            145                 150                 155
Pro Asn Pro Asn Ala His Leu Pro Val Val Arg Ser Thr Gln Pro Ile
160                 165                 170                 175

Arg Asn Leu Thr Gly Arg Ala Ile Pro Ala Ser Cys Ala Ser Thr Ile
                180                 185                 190

Thr Pro Ala Cys Leu Gln Ala Ile Tyr Gly Ile Pro Thr Thr Lys Ala
                195                 200                 205

Thr Gln Ser Ser Asn Lys Leu Ala Val Ser Gly Phe Ile Asp Gln Phe
            210                 215                 220

Ala Asn Lys Ala Asp Leu Lys Ser Phe Leu Ala Gln Phe Arg Lys Asp
            225                 230                 235

Ile Ser Ser Ser Thr Thr Phe Ser Leu Gln Thr Leu Asp Gly Gly Glu
240                 245                 250                 255

Asn Asp Gln Ser Pro Ser Glu Ala Gly Ile Glu Ala Asn Leu Asp Ile
                260                 265                 270

Gln Tyr Thr Val Gly Leu Ala Thr Gly Val Pro Thr Thr Phe Ile Ser
                275                 280                 285

Val Gly Asp Asp Phe Gln Asp Gly Asn Leu Glu Gly Phe Leu Asp Ile
            290                 295                 300

Ile Asn Phe Leu Leu Gly Glu Ser Asn Pro Pro Gln Val Leu Thr Thr
305                 310                 315

Ser Tyr Gly Gln Asn Glu Asn Thr Ile Ser Ala Lys Leu Ala Asn Gln
320                 325                 330                 335

Leu Cys Asn Ala Tyr Ala Gln Leu Gly Ala Arg Gly Thr Ser Ile Leu
                340                 345                 350

Phe Ala Ser Gly Asp Gly Gly Val Ser Gly Ser Gln Ser Ala His Cys
                355                 360                 365

Ser Asn Phe Val Pro Thr Phe Pro Ser Gly Cys Pro Phe Met Thr Ser
            370                 375                 380

Val Gly Ala Thr Gln Gly Val Ser Pro Glu Thr Ala Ala Phe Ser
385                 390                 395

Ser Gly Gly Phe Ser Asn Val Phe Gly Ile Pro Ser Tyr Gln Ala Ser
400                 405                 410                 415

Ala Val Ser Gly Tyr Leu Ser Ala Leu Gly Ser Thr Asn Ser Gly Lys
                420                 425                 430

Phe Asn Arg Ser Gly Arg Gly Phe Pro Asp Val Ser Thr Gln Gly Val
                435                 440                 445

Asp Phe Gln Ile Val Ser Gly Gly Gln Thr Ile Gly Val Asp Gly Thr
            450                 455                 460

Ser Cys Ala Ser Pro Thr Phe Ala Ser Val Ile Ser Leu Val Asn Asp
465                 470                 475

Arg Leu Ile Ala Ala Gly Lys Ser Pro Leu Gly Phe Leu Asn Pro Phe
480                 485                 490                 495

Leu Tyr Ser Ser Ala Gly Lys Ala Ala Leu Asn Asp Val Thr Ser Gly
                500                 505                 510

Ser Asn Pro Gly Cys Ser Thr Asn Gly Phe Pro Ala Lys Ala Gly Trp
                515                 520                 525

Asp Pro Val Thr Gly Leu Gly Thr Pro Asn Phe Ala Lys Leu Leu Thr
            530                 535                 540

Ala Val Gly Leu
            545
```

<210> SEQ ID NO 15

```
<211> LENGTH: 640
<212> TYPE: PRT
<213> ORGANISM: Kionochaeata sp
<220> FEATURE:
<221> NAME/KEY: SIGNAL
<222> LOCATION: (1)..(18)
<220> FEATURE:
<221> NAME/KEY: mat_peptide
<222> LOCATION: (19)..(640)

<400> SEQUENCE: 15
```

Met Arg Thr Ser Ser Ile Leu Ser Leu Ala Leu Gly Ala Ser Val Ala
              -15                  -10                -5

Gln Ala Ala Val Ser Pro Ala Asp Val Leu Ala Val Glu Lys Arg
 -1  1              5                      10

Val Asp Pro Ala Ser Gly Leu Glu Ala Arg Ser Ile Trp Asp Thr Ile
15                20                25                30

Trp Asp Asp Ile Lys Ser Ala Ala Asp Cys Thr Ala Cys Glu Ala Val
            35                40                45

Leu Thr Leu Leu Lys Gly Val Ala Phe Gly Asp Ser Phe Phe Val
        50                55                60

Glu Val Leu Thr Glu Ile Cys Asp Leu Ser Gly Ala Glu Asp Asp
        65                70                75

Val Cys Ser Gly Val Leu Ser Leu Glu Gly Pro Ile Leu Ala Asn Asp
80                85                90

Ile Arg Lys Met Ser Ile Gly Ser Lys Thr Ser Glu Leu Phe Cys Ile
95                100               105              110

Thr Phe Leu Gly Leu Cys Ser Tyr Pro Asp Val Asp Ala Tyr Lys Val
            115              120              125

Pro Phe Pro Thr Ala Ser Ser Ala Ala Thr Arg Pro Val Ser Ser Gly
        130              135              140

Lys Asp Pro Leu Tyr Val Val His Phe Ser Asp Ile His Ile Asp Pro
        145              150              155

Phe Tyr Val Ala Gly Ser Ala Ser Asn Cys Thr Lys Pro Ile Cys Cys
        160              165              170

Arg Asp Tyr Thr Ser Ala Ser Ser Pro Gly Asn Asn Asp Ser Pro Ala
175                180                185              190

Gly Pro Tyr Gly Asp His Asn Cys Asp Val Pro Tyr Ser Leu Glu Asp
            195              200              205

Ser Met Tyr Ala Ala Ile Lys Glu Leu Val Pro Asn Ala Ala Phe Gly
        210              215              220

Ile Phe Thr Gly Asp Ile Val Asp His Ala Val Trp Asn Thr Ser Glu
        225              230              235

Ser Gln Asn Ile Ile Asp Met Asn Asp Ala Tyr Ser Arg Met Lys Ser
        240              245              250

Ser Gly Met Leu Pro Ala Ile Phe Ala Thr Ala Gly Asn His Glu Ala
255                260                265              270

Ser Pro Val Asn Ala Phe Pro Pro Ala Val Gly Lys Glu Ser Gln
            275              280              285

Trp Val Tyr Asp Thr Leu Ala Ser Asp Trp Ser Gln Trp Ile Gly Ala
            290              295              300

Ser Ala Ala Ser Ser Val Glu Ser Gln Gly Ala Tyr Ser Val Leu Tyr
        305              310              315

Gly Ser Thr Lys Leu Arg Ile Ile Ser Leu Asn Thr Asn Met Tyr Tyr
320                325                330

Ile Glu Asn Phe Tyr Leu Tyr Glu Pro Thr Met Glu Thr Asp Pro Ala

```
                335                 340                 345                 350
        Gly Gln Phe Ala Trp Leu Val Ser Glu Leu Ser Ala Ala Glu Ala Ala
                        355                 360                 365

Gly Glu Arg Val Trp Ile Ile Gly His Met Pro Met Gly Leu Ser Asp
                        370                 375                 380

Ala Phe His Asn Pro Ser Asn Tyr Phe Asp Gln Ile Val Asn Arg Tyr
                        385                 390                 395

Gln Ala Thr Ile Ala Ala Leu Phe Phe Gly His Thr His Glu Asp His
                        400                 405                 410

Phe Gln Ile Ser Tyr Ser Asp Tyr Gly Ala Gln Thr Ala Ala Asn Ala
        415                 420                 425                 430

Arg Ala Ile Ser Tyr Ile Met Pro Ser Leu Thr Pro Thr Ser Gly His
                        435                 440                 445

Pro Thr Phe Arg Val Tyr Ala Val Asp Pro Glu Thr Phe Gly Val Leu
                        450                 455                 460

Asp Ala Thr Thr Tyr Tyr Ala Asp Met Gly Leu Ala Ser Tyr Gln Thr
                        465                 470                 475

Ala Gly Pro Thr Trp Lys Pro Tyr Tyr Ser Ala Arg Asp Ala Tyr Gly
                        480                 485                 490

Gly Leu Val Asp Pro Pro Leu Pro Ala Gly Ala Glu Leu Thr Pro Ala
        495                 500                 505                 510

Phe Trp His Asn Val Thr Ala Ala Leu Ala Ala Asn Gln Thr Ser Phe
                        515                 520                 525

Asp Ala Tyr Tyr Ala Arg Lys Thr Arg Gly Trp Asp Val Ala Pro Cys
                        530                 535                 540

Thr Gly Ala Cys Ala Thr Ala Glu Ile Cys Ala Leu Arg Ala Ala Arg
                        545                 550                 555

Ala Gln Asn Asn Cys Val Val Pro Thr Pro Gly Val His Phe Ser Lys
                        560                 565                 570

Arg Ala Thr Asp Glu Ala Glu Gly Ala His His Arg Asp Glu Cys Gly
        575                 580                 585                 590

Ile Ser Val Ala Arg Asn Ser Leu Ser Ser Leu Val Ala Arg Arg Glu
                        595                 600                 605

Ala Leu Glu His Leu Glu Ser Arg Leu Val Glu Arg Arg Ala Val
                        610                 615                 620

<210> SEQ ID NO 16
<211> LENGTH: 610
<212> TYPE: PRT
<213> ORGANISM: Penicillium emersonii
<220> FEATURE:
<221> NAME/KEY: SIGNAL
<222> LOCATION: (1)..(16)
<220> FEATURE:
<221> NAME/KEY: mat_peptide
<222> LOCATION: (17)..(610)

<400> SEQUENCE: 16

Met Arg Val Leu Ala Leu Ile Ala Ala Leu Ala Thr Val Ala Thr Ala
                -15                 -10                 -5                  -1

Ser Ala Pro Tyr Asp Lys Arg Asp Leu Ala Gln Glu Ile Trp Asp Asp
        1                   5                   10                  15

Ile Lys Asn Ala Val Asp Cys Ala Gly Cys Gln Val Val Leu Thr Ala
                        20                  25                  30

Leu Lys Gly Val Ala Asp Leu Gly Thr Thr Ala Leu Val Asp Val Leu
                        35                  40                  45
```

```
Thr Glu Val Cys Asn Ile Ser Gly Lys Glu Asp Ser Asp Val Cys Ser
         50                   55                  60
Gly Ile Ile Ser Arg Glu Gly Pro Val Leu Asp Tyr Val Leu Gln His
 65              70                   75                      80
Leu Asp Ile Gly Ser His Thr Ser Gln Val Ile Cys Ala Ser Ala Phe
                     85                  90                  95
Gly Leu Cys Gln Tyr Pro Glu Val Arg Pro Tyr Asn Leu Thr Phe Pro
                100                 105                110
Lys Pro Lys Pro Asn Thr Thr Arg Pro Glu Pro Ser Gly Glu Ser Pro
            115                 120                 125
Ile Gln Val Val His Phe Ser Asp Thr His Val Asp Leu Ser Tyr Glu
        130                 135                 140
Thr Gly Ser Asn Tyr Asn Cys Thr Lys Pro Ile Cys Cys Arg Pro Tyr
145                 150                 155                 160
Thr Ala Glu Asp Ala Pro Gly Asn Thr Thr Thr Pro Cys Gly Pro Tyr
                165                 170                 175
Gly Asn Thr Lys Cys Asp Ala Pro Leu Ser Leu Glu Glu Ser Met Phe
                180                 185                 190
Ala Ala Ile Lys Ala Leu Asn Pro Gln Pro Ala Phe Ser Ile Tyr Thr
            195                 200                 205
Gly Asp Val Val Ala His Asp Ile Trp Leu Val Asp Gln Asn Glu Val
210                 215                 220
Ile Glu Asp Leu Asn Ala Thr Tyr Asp Arg Met Ala Gly Leu Gly Leu
225                 230                 235                 240
Val Tyr Ala Ala Ile Gly Asn His Asp Thr Ala Pro Val Asn Asp Leu
                245                 250                 255
Pro Thr Ser Asn Ile Pro Ser Glu Tyr Ser Ala Asn Trp Thr Tyr Glu
                260                 265                 270
Ala Leu Ser Tyr Asp Phe Thr Met Leu Thr Gln Ser Ala Ser Ala Gln
            275                 280                 285
Thr Ala Ala Asn Tyr Gly Ser Tyr Ser Ala Ile Tyr Pro Gly Ser Tyr
        290                 295                 300
Gly Thr Asp Leu Arg Val Ile Ser Tyr Asn Ser Ile Phe Tyr Tyr Val
305                 310                 315                 320
Asp Asn Phe Trp Ala Tyr Gln Asp Pro Met Glu Phe Asp Pro Asp Gly
                325                 330                 335
Gln Leu Ala Trp Leu Ile Asn Glu Leu Gln Glu Ala Glu Thr Ala Gly
                340                 345                 350
Gln Arg Val Trp Ile Ile Ala His Val Pro Thr Gly Thr Ser Asp His
            355                 360                 365
Phe His Asp Tyr Ser His Tyr Phe Asp Gln Ile Val Gln Arg Tyr Glu
        370                 375                 380
Ala Thr Ile Ala Ala Leu Phe Tyr Gly His Thr His Ile Asp Gln Phe
385                 390                 395                 400
Gln Ile Ser Tyr Ser Asn Tyr Ser Asn Arg Ala Phe Asp Thr Ala Thr
                405                 410                 415
Ala Ile Gly Tyr Ile Met Pro Ser Leu Thr Pro Thr Ser Gly Pro Pro
                420                 425                 430
Thr Phe Arg Val Tyr Asp Val Asp Pro Lys Thr Phe Ala Val Leu Asp
            435                 440                 445
Phe Thr Asn Tyr Ile Ala Asn Ile Ser Asp Pro Ala Phe Gln Ser Gly
450                 455                 460
Pro Ser Trp Gln Lys Tyr Tyr Ser Ala Lys Glu Thr Tyr Gly Ser Leu
```

```
465                 470                 475                 480

Leu Ser Pro Pro Val Thr Asp Pro Thr Ala Glu Leu Thr Pro Ala Phe
                485                 490                 495

Trp His Asn Val Thr Val Ala Phe Glu Gln Asp Asn Ala Thr Phe Gln
            500                 505                 510

Glu Tyr Trp Ala Arg Gln Thr Arg Gly Tyr Asp Val Ser Ser Cys Thr
        515                 520                 525

Gly Ser Cys Ile Thr Gln Ala Ile Cys Gly Leu Arg Ala Gly Asp Ala
    530                 535                 540

Gln Tyr Asn Cys Val Thr Pro Thr Pro Gly Phe Asn Phe Ala Lys Arg
545                 550                 555                 560

Asp Thr Ser Asn Pro Lys Gln Ala Leu Ser His Val Glu Lys Cys Glu
                565                 570                 575

Gly Ser Gly Leu Leu Gly Leu Leu Arg Arg Met Val Ala Asp Ser Lys
            580                 585                 590

Ser Ser

<210> SEQ ID NO 17
<211> LENGTH: 278
<212> TYPE: PRT
<213> ORGANISM: Bacillus thuringensis
<220> FEATURE:
<221> NAME/KEY: SIGNAL
<222> LOCATION: (1)..(33)
<220> FEATURE:
<221> NAME/KEY: mat_peptide
<222> LOCATION: (34)..(278)

<400> SEQUENCE: 17

Met Lys His His Arg Phe Arg Thr Asn Leu Leu Ser Ala Leu Ser Val
            -30                 -25                 -20

Ser Ser Ile Val Ile Thr Ser Ile Ile Gly Ser Thr Gln Thr Thr Tyr
        -15                 -10                 -5

Ala Trp Ser Ala Asp Ala Pro His Asp Pro Asn Gln Ser Thr His Leu
-1  1               5                   10                  15

Phe Ile Val Asn Gly Ala Val Asn Leu Val Ala Asn Asn Thr Asp Pro
                20                  25                  30

Gln Ile Asn Lys Pro Thr Ala Leu Leu Gln Gln Trp Arg Ser Gln Trp
            35                  40                  45

Glu Gln Gly Leu Tyr Asp Ala Asp His Leu Asn Pro Tyr Tyr Asp Ser
        50                  55                  60

Gly Thr Phe Met Ser His Phe Tyr Asp Pro Asp Thr Gln Thr Asn Tyr
    65                  70                  75

Ala Gly Leu Ser Tyr Pro Thr Ala Arg Gln Thr Gly Ala Lys Tyr Phe
80                  85                  90                  95

Thr Ile Ala Ser Asn Asp Tyr Gln Ala Gly Asp Met Ser Asp Ala Phe
                100                 105                 110

Tyr Asn Leu Gly Leu Ser Leu His Tyr Phe Thr Asp Val Thr Met Pro
            115                 120                 125

Leu His Ala Gly Asn Ile Ser Asn Leu Asp His Glu Ala Pro Gly Tyr
        130                 135                 140

His Ala Lys Leu Glu Ala Tyr Ala Glu Ser Ile Gln Asn Gln Val Thr
    145                 150                 155

Pro Pro Thr Ala Gly Leu Tyr Asn Trp Val Ser Pro Asn Asp Pro Glu
160                 165                 170                 175

Leu Trp Ile His Gln Ala Ala Val Gln Ala Lys Ser Val Leu Pro Gln
```

-continued

```
                180                 185                 190
Val Trp Asn Ser Asp Ile Thr Ser Trp Phe Trp Glu Ala Ala Phe Ser
            195                 200                 205

Asn Tyr Tyr Ser Gln Gln Trp His Asn Ala Val Thr Thr Pro Val Leu
        210                 215                 220

Asn Gln Leu Ser Gln Ala Glu Ala Glu Thr Ala Gly Tyr Ile Asp Leu
    225                 230                 235

Phe Phe Arg Val Asn Gly
240                 245
```

PROCESS OF EXTRACTING OIL FROM THIN STILLAGE

CROSS-REFERENCE TO RELATED APPLICATIONS

This application is a continuation of U.S. application Ser. No. 16/787,203 filed Feb. 11, 2020, now allowed, which is a continuation of U.S. application Ser. No. 16/062,519 filed Jun. 14, 2018, now U.S. Pat. No. 10,597,645, which is a 35 U.S.C. 371 national application of international application no. PCT/US2016/067080 filed Dec. 16, 2016, which claims priority or the benefit under 35 U.S.C. 119 of U.S. application nos. 62/271,182, 62/271,063, 62/324,107 and 62/430,695, filed Dec. 22, 2015, Dec. 22, 2015, Apr. 18, 2016 and Dec. 6, 2016, respectively, the contents of which are fully incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 9, 2023 is named SQ.txt and is 57.3 KB in size and has 58,750 bytes.

FIELD OF THE INVENTION

The present invention relates to processes of extracting/recovering oil from thin stillage and/or syrup at the backend of a fermentation product production process based on starch-containing material.

BACKGROUND OF THE INVENTION

Fermentation products, such as ethanol, are typically produced by first grinding starch-containing material in a dry-grind or wet-milling process, then degrading the material into fermentable sugars using enzymes and finally converting the sugars directly or indirectly into the desired fermentation product using a fermenting organism. Liquid fermentation products are recovered from the fermented mash (often referred to as "beer mash"), e.g., by distillation, which separate the desired fermentation product from other liquids and/or solids. The remaining fraction is referred to as "whole stillage". The whole stillage is dewatered and separated into a solid and a liquid phase, e.g., by centrifugation. The solid phase is referred to as "wet cake" (or "wet grains") and the liquid phase (supernatant) is referred to as "thin stillage". Wet cake and thin stillage contain about 35% and 7% solids, respectively. Dewatered wet cake is dried to provide "Distillers Dried Grains" (DDG) used as nutrient in animal feed. Thin stillage is typically evaporated to provide condensate and syrup or may alternatively be recycled directly to the slurry tank as "backset". Condensate may either be forwarded to a methanator before being discharged or may be recycled to the slurry tank. The syrup may be blended into DDG or added to the wet cake before drying to produce DDGS (Distillers Dried Grain with Solubles). An increasing number of ethanol plants extract oil from the thin stillage and/or syrup/evaporated centrate as a by-product for use in biodiesel production or other biorenewable products.

Much of the work in oil recovery/extraction from fermentation product production processes has focused on improving the extractability of the oil from the thin stillage. Effective removal of oil is often accomplished by hexane extraction. However, the utilization of hexane extraction has not seen widespread application due to the high capital investment required. Therefore, other processes that improve oil extraction from fermentation product production processes have been explored.

WO 2011/126897 (Novozymes) discloses processes of recovering oil by converting starch-containing materials into dextrins with alpha-amylase; saccharifying with a carbohydrate source generating enzyme to form sugars; fermenting the sugars using fermenting organism; wherein the fermentation medium comprises a hemicellulase; distilling the fermentation product to form whole stillage; separating the whole stillage into thin stillage and wet cake; and recovering oil from the thin stillage. The fermentation medium may further comprise a protease.

WO 2014/209789 (Novozymes) discloses processes of recovering oil after liquefaction and/or from thin stillage and/or syrup/evaporated centrate from a fermentation product production process by adding a thermostable protease to the whole stillage, thin stillage and/or syrup It is an object of the present invention to provide improved processes for increasing the amount of recoverable oil from fermentation product production processes.

SUMMARY OF THE INVENTION

The object of the present invention is to provide improved processes of extracting or recovering oil at the backend of a fermentation product production process, such as especially an ethanol production process.

Therefore, in the first aspect the invention relates to processes of recovering oil, comprising (a) converting a starch-containing material into dextrins with an alpha-amylase;

(b) saccharifying the dextrins using a carbohydrate source generating enzyme to form a sugar;

(c) fermenting the sugar in a fermentation medium into a fermentation product using a fermenting organism;

(d) recovering the fermentation product to form a whole stillage;

(e) separating the whole stillage into thin stillage and wet cake;

(e') optionally concentrating the thin stillage into syrup;

(f) recovering oil from the thin stillage and/or optionally the syrup, wherein a protease and a phospholipase are present and/or added during steps (a) to (c).

In an embodiment the protease and the phospholipase are present and/or added during step (b) and/or step (c). If step (a) is carried out above the initial gelatinization temperature, such as between 70-100° C., preferably between 80-90° C., such as around 85° C., a thermostable protease may also be present in and/or added in starch-containing material converting step (a).

Steps (b) and (c) may be carried out simultaneously or sequentially. In embodiments steps (a), (b) and (c) are carried our simultaneously or sequentially. When steps (a), (b) and (c), or steps (b) and (c), are carried out simultaneously, the temperature is below the initial gelatinization temperature, such as between 20-60° C., preferably between 25-40° C., such as around 32° C.

The oil may according to the invention be recovered from the thin stillage and/or syrup/evaporated centrate, e.g., by extraction, such as hexane extraction, or by using another oil recovery technology well-known in the art.

In an embodiment the protease added in steps (a)-(c) carried out at a temperature below the initial gelatinization temperature; or steps (b) and/or (c) carried out at a temperature below the initial gelatinization temperature, where step (a) is carried out at a temperature above the initial gelatinization temperature, may preferably be a protease of the peptidase family S53 protease, e.g., derived from a strain of *Meripilus*, preferably a strain of *Meripilus giganteus*, e.g., the one shown as SEQ ID NO: 14 herein; or the mature protease derived from *Thermoascus aurantiacus* shown in SEQ ID NO: 3 herein. The protease is in accordance with the invention combined with a phospholipase, e.g., derived from *Kionochaeata* sp. (e.g., SEQ ID NO: 15), *Penicillium emersonii* (e.g., SEQ ID NO: 16) and *Bacillus thuringensis* (e.g., SEQ ID NO: 17), with phospholipase from *Penicillium emersonii* being preferred.

In an embodiment, the protease added in step (a) carried out above the initial gelatinization temperature may be any protease having a thermostability value, as defined herein, of more than 20% determined as Relative Activity. "Relative Activity" and "Remaining Activity" are determined as described in Example 1. In an embodiment the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. In an embodiment the protease added in step (a) carried out above the initial gelatinization temperature has a themostability of above 90%, above 100% at 85° C. as determined using the Zein-BCA assay as disclosed in Example 2.

In an embodiment said protease added in step (a) at a temperature above the initial gelatinization temperature is a thermostable variant of the parent protease derived from *Thermoascus aurantiacus* shown in SEQ ID NO: 3 herein, classified as EC 3.4.24.39, or one having a sequence identity thereto of at least 60%, at least 70%, at least 80%, at least 90%, at least 95%, at least 96%, at least 97%, at least 98%, at least 99%, but less than 100%.

This includes the thermostable protease variants of the parent protease shown in SEQ ID NO: 3, having one of the following set of substitutions:

D79L+S87P+A112P+D142L
D79L+Y82F+S87P+A112P+D142L
S38T+D79L+S87P+A112P+A126V+D142L
D79L+Y82F+S87P+A112P+A126V+D142L
A27K+D79L+S87P+A112P+A126V+D142L
S49P+D79L+S87P+A112P+D142L
S50P+D79L+S87P+A112P+D142L
D79L+S87P+D104P+A112P+D142L
D79L+Y82F+S87G+A112P+D142L
570V+D79L+Y82F+S87G+Y97W+A112P+D142L
D79L+Y82F+S87G+Y97W+D104P+A112P+D142L
S70V+D79L+Y82F+S87G+A112P+D142L
D79L+Y82F+S87G+D104P+A112P+D142L
D79L+Y82F+S87G+A112P+A126V+D142L
Y82F+S87G+S70V+D79L+D104P+A112P+D142L
Y82F+S87G+D79L+D104P+A112P+A126V+D142L
A27K+D79L+Y82F+S87G+D104P+A112P+A126V+D142L
A27K Y82F S87G D104P A112P A126V D142L
A27K D79L Y82F D104P A112P A126V D142L
A27K Y82F D104P A112P A126V D142L

In a preferred embodiment the thermostable protease is a variant of the parent protease (e.g., derived from *Thermoascus aurantiacus*) shown in SEQ ID NO: 3 herein with the following substitutions:

A27K+D79L+Y82F+S87G+D104P+A112P+A126V+D142 L;
D79L+Y82F+S87G+A112P+D142L;
Y82F+S87G+S70V+D79L+D104P+A112P+D142 L;
Y82F+S87G+D79L+D104P+A112P+A126V+D142L
(using SEQ ID NO: 3 herein for numbering).

All of these protease variants have a higher thermostability value (as defined herein) than the (wild-type) parent protease shown in SEQ ID NO: 3 herein.

In an embodiment the protease added in step (a) carried out above the initial gelatinization temperature may be a filamentous fungus, e.g., a protease classified as EC 3.4.23.23, such as derived from a strain of *Rhizomucor*, such as *Rhizomucor miehei*, such as the protease shown in SEQ ID NO: 9 herein or one having a sequence identity thereto of at least 60%, at least 70%, at least 80%, at least 90%, at least 95%, at least 96%, at least 97%, at least 98%, at least 99%.

In an embodiment the protease added in step (a) carried out above the initial gelatinization temperature is a thermostable protease derived from the bacterium, e.g., classified as EC 3.4.21.62, such as *Pyrococcus furiosus*, such as the protease shown in SEQ ID NO: 4 herein or a protease having a sequence identity thereto of at least 60%, at least 70%, at least 80%, at least 90%, at least 95%, at least 96%, at least 97%, at least 98%, at least 99%.

In an embodiment the protease added in step (a) carried out above the initial gelatinization temperature may be a bacterial serine protease, such as one derived from a strain of *Thermobifida*, such as *Thermobifida fusca*, such as the protease shown in SEQ ID NO: 10 herein or one having a sequence identity thereto of at least 60%, at least 70%, at least 80%, at least 90%, at least 95%, at least 96%, at least 97%, at least 98%, at least 99%.

In an embodiment of the invention the protease is added in a concentration of 0.01-100, such 0.1-10 micro g/g DS.

In another aspect the invention relates to the use of a protease and a phospholipase, in particular phospholipase C for oil recovery from thin stillage and/or syrup at the backend of a fermentation product production process based on starch-containing material.

BRIEF DESCRIPTION OF THE DRAWING

FIG. 1 schematically shows an ethanol production process. Oil may be recovered/extracted from the thin stillage and/or the syrup/centrate. The boxes in the FIGURE indicate where oil may be recovered/extracted.

DETAILED DESCRIPTION OF THE INVENTION

The object of the present invention is to provide improved processes of extracting or recovering oil at the backend of a fermentation product production process, such as especially an ethanol production process.

The invention relates to the use of a protease and a phospholipase in a fermentation product production process. The use of both enzymes in combination improves the extraction or recovery of oil. This may be due to the reduction in gumming or emulsification of the oil, allowing for an improved yield and/or quality of the oil.

Therefore, in the first aspect the invention relates to processes of recovering oil, comprising
(a) converting a starch-containing material into dextrins with an alpha-amylase;
(b) saccharifying the dextrins using a carbohydrate source generating enzyme to form a sugar;
(c) fermenting the sugar in a fermentation medium into a fermentation product using a fermenting organism;

(d) recovering the fermentation product to form a whole stillage;

(e) separating the whole stillage into thin stillage and wet cake;

(e') optionally concentrating the thin stillage into syrup;

(f) recovering oil from the thin stillage and/or optionally the syrup, wherein a protease and a phospholipase are present and/or added during steps (a) to (c).

In an embodiment the protease and the phospholipase are present and/or added during steps (b) and/or (c).

In an embodiment the protease and the phospholipase are added sequentially or simultaneously.

In an embodiment the protease, added during steps (a) to (c), preferably steps (b) and/or (c), is a serine protease, such as a peptidase family S53 protease. Serine proteases of the peptidase family S53 comprises two different types of peptidases: tripeptidyl aminopeptidases (exo-type) and endo-peptidases; as described in 1993, Biochem. J. 290:205-218 and in MEROPS protease database, release, 9.4 (31 Jan. 2011) (www.merops.ac.uk). The database is described in Rawlings, N. D., Barrett, A. J. and Bateman, A., 2010, "MEROPS: the peptidase database", Nucl. Acids Res. 38: D227-D233.

In a preferred embodiment the protease is a peptidase family S53 protease derived from a strain of *Meripilus*, preferably a strain of *Meripilus giganteus*. In an embodiment the protease is the mature sequence from *Meripilus giganteus* protease 3 (peptidase family S53 protease) concerned in Example 2 in WO 2014/037438 and/or shown as SEQ ID NO: 14 herein.

According to the invention the protease present and/or added in steps (a) to (c), preferably steps (b) and/or (c), may be a protease (e.g., derived from *Meripilus giganteus*) having the amino acid sequence set out in SEQ ID NO: 14 herein, or is a protease which has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 14 herein.

In another embodiment the protease present and/or added in steps (a) to (c), preferably (b) and/or (c), may be a protease (e.g., derived from *Thermoascus aurantiacus*) having the amino acid sequence set out in SEQ ID NO: 3 herein, or is a protease which has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 3 herein.

According to the invention a phospholipase is present and/or added in steps (a) to (c), preferably step (b) and/or (c) in combination with the protease. In case the temperature in step (a) is below the initial gelatinization temperature the phospholipase may be added in step (a). If the temperature in step (a) is above the initial gelatinization temperature the phospholipase is preferably added in steps (b) and/or (c).

In a preferred embodiment the phospholipase is a phospholipase C.

Examples of phospholipases, present and/or added in steps (a) to (c), preferably steps (b) and/or (c), includes those having the amino acid sequences of SEQ ID NO: 15 herein; SEQ ID NO: 16 herein; and SEQ ID NO: 17 herein. Preferred is the phospholipase having the amino acid sequence of SEQ ID NO: 16 herein.

In an embodiment the phospholipase may be derived from *Kionochaeta*, such as the phospholipase shown in SEQ ID NO: 15 herein or one having a sequence identity thereto of at least 60%, at least 70%, at least 80%, at least 90%, at least 95%, at least 96%, at least 97%, at least 98%, at least 99%.

In a preferred embodiment the phospholipase is derived from *Penicillium*, such as the phospholipase shown in SEQ ID NO: 16 herein or one having a sequence identity thereto of at least 60%, at least 70%, at least 80%, at least 90%, at least 95%, at least 96%, at least 97%, at least 98%, at least 99%.

In an additional embodiment the phospholipase may be derived from *Bacillus*, such as the phospholipase shown in SEQ ID NO: 17 herein or one having a sequence identity thereto of at least 60%, at least 70%, at least 80%, at least 90%, at least 95%, at least 96%, at least 97%, at least 98%, at least 99%.

In an embodiment the process of recovering oil of the invention, comprises:

(a) converting a starch-containing material into dextrins with an alpha-amylase at a temperature above the initial gelatinization temperature;

(b) saccharifying the dextrins using a carbohydrate source generating enzyme to form a sugar;

(c) fermenting the sugar in a fermentation medium into a fermentation product using a fermenting organism;

(d) recovering the fermentation product to form a whole stillage;

(e) separating the whole stillage into thin stillage and wet cake;

(e') optionally concentrating the thin stillage into syrup;

(f) recovering oil from the thin stillage and/or optionally the syrup, wherein a protease and a phospholipase are present and/or added during steps (b) and/or (c).

In an embodiment, a protease may be added together with the alpha-amylase in step (a) carried out at a temperature above the initial gelatinization temperature.

The protease may be any protease having a thermostability value, as defined herein, of more than 20% and the Example 1. In an embodiment the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

In one embodiment the protease is a thermostable variant of the protease derived from *Thermoascus aurantiacus* shown in SEQ ID NO: 3 herein, or one having a sequence identity thereto of at least 90%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

In one embodiment the protease is a thermostable variant of the protease derived from *Thermoascus aurantiacus* shown in SEQ ID NO: 3 herein, or one having a sequence identity thereto of at least 95%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

In one embodiment the protease is a thermostable variant of the protease derived from *Thermoascus aurantiacus* shown in SEQ ID NO: 3 herein, or one having a sequence identity thereto of at least 99%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

In an embodiment the protease is a thermostable variant of the protease derived *Thermoascus aurantiacus* shown in SEQ ID NO: 3 herein, or one having a sequence identity thereto of at least 60%, at least 70%, at least 80%, at least 90%, at least 95%, at least 96%, at least 97%, at least 98%, at least 99%.

Examples of suitable protease variants are disclosed in the Examples below. In a preferred embodiment the protease variant is selected from the group of variants comprising the following substitutions:

A27K+D79L+Y82F+S87G+D104P+A112P+A126V+ D142L;

D79L+Y82F+S87G+A112P+D142L;

Y82F+S87G+S70V+D79L+D104P+A112P+D142L;

Y82F+S87G+D79L+D104P+A112P+A126V+D142L (using SEQ ID NO: 3 herein for numbering).

All suitable protease variants have higher thermostability value (as defined herein) than the wild-type parent protease shown in SEQ ID NO: 3 herein.

In an embodiment the protease is a filamentous fungus, e.g., derived from a strain of *Rhizomucor*, such as *Rhizomucor miehei*, such as the protease shown in SEQ ID NO: 9 herein or one having a sequence identity thereto of at least 60%, at least 70%, at least 80%, at least 90%, at least 95%, at least 96%, at least 97%, at least 98%, at least 99%.

In an embodiment the protease is derived from a strain of *Rhizomucor miehei*, such as the protease shown in SEQ ID NO: 9 herein, or one having a sequence identity thereto of at least 90%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. (See Example 3).

In a preferred embodiment the protease added in step (a) carried out at a temperature above the initial gelatinization temperature is a thermostable protease derived from the bacterium *Pyrococcus furiosus*, such as the protease shown in SEQ ID NO: 4 herein, or one having sequence identity thereto of at least 60%, at least 70%, at least 80%, at least 90%, at least 95%, at least 96%, at least 97%, at least 98%, at least 99%.

The *Pyrococcus furiosus* protease shown in SEQ ID NO: 4 herein is a thermostable bacterial protease. A commercial *Pyrococcus furiosus* protease product (Pfu S) from Takara Bio InC. (Japan) have been found to have a thermostability value of 110% (80° C./70° C.) and 103% (90° C./70° C.) at pH 4.5 determined as described in Example 1 herein.

In an embodiment the protease is a thermostable protease derived from the bacterium *Pyrococcus furiosus*, such as the protease shown in SEQ ID NO: 4 herein, or one having a sequence identity thereto of at least 90%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. (See Example 3).

In an embodiment the protease is a thermostable protease derived from the bacterium *Pyrococcus furiosus*, such as the protease shown in SEQ ID NO: 4 herein, or one having a sequence identity thereto of at least 95%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. (See Example 3).

In an embodiment the protease is a thermostable protease derived from the bacterium *Pyrococcus furiosus*, such as the protease shown in SEQ ID NO: 4 herein, or one having a sequence identity thereto of at least 99%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. (See Example 3).

In an additional embodiment the protease is a bacterial serine protease, such as derived from a strain of *Thermobifida*, such as *Thermobifida fusca*, such as the protease shown in SEQ ID NO: 10 herein or one having a sequence identity thereto of at least 60%, at least 70%, at least 80%, at least 90%, at least 95%, at least 96%, at least 97%, at least 98%, at least 99% (See Example 3).

In one embodiment the protease is derived from a strain of *Thermobifida*, such as *Thermobifida fusca*, such as the protease shown in SEQ ID NO: 10 herein, or one having a sequence identity thereto of at least 90%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. (See Example 3).

In one embodiment the protease is derived from a strain of *Thermobifida*, such as *Thermobifida fusca*, such as the protease shown in SEQ ID NO: 10 herein, or one having a sequence identity thereto of at least 95%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. (See Example 3).

In one embodiment the protease is derived from a strain of *Thermobifida*, such as *Thermobifida fusca*, such as the protease shown in SEQ ID NO: 10 herein, or one having a sequence identity thereto of at least 99%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. (See Example 3).

When step (a) is carried out as a liquefaction step at high temperatures, i.e., above the initial gelatinization temperature, such as at temperatures between 70-100° C., preferably between 80-90° C., such as around 85° C., the alpha-amylase is preferably a bacterial alpha-amylase.

In a preferred embodiment the alpha-amylase used in step (a), when the temperature in step (a) is above the initial gelatinization temperature, is a bacterial alpha-amylase.

Especially preferred are bacterial alpha-amylases derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein, in particular a *Bacillus stearothermophilus* alpha-amylase truncated, preferably to be from 485-495 amino acids long, such as around 491 amino acids long.

In a preferred embodiment the bacterial alpha-amylase is selected from the group of *Bacillus stearothermophilus* alpha-amylase variants comprising a deletion of one or two amino acids at any of positions R179, G180, I181 and/or G182, preferably the double deletion disclosed in WO 96/23873—see, e.g., page 20, lines 1-10 (hereby incorporated by reference), preferably corresponding to deletion of positions I181+G182 compared to the amino acid sequence of *Bacillus stearothermophilus* alpha-amylase set forth as SEQ ID NO: 3 disclosed in WO 99/19467 or SEQ ID NO: 1 herein or the deletion of amino acids R179 and G180 using SEQ ID NO: 3 in WO 99/19467 or SEQ ID NO: 1 herein for numbering.

In an embodiment the bacterial alpha-amylase is selected from the group of *Bacillus stearothermophilus* alpha-amylase variants with the one of the following set of mutations:

I181*+G182*;
I181*+G182*+N193F;
preferably
I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A Q89R+E129V+K177L+R179E+Q254S+M284V; and
I181*+G182*+N193F+E129V+K177L+R179E+K220P+N224L+S242Q+Q254S (using SEQ ID NO: 1 for numbering).

The parent *Bacillus stearothermophilus* alpha-amylase may be the one shown in SEQ ID NO: 1 or may be one having sequence identity thereto of at least 60%, at least 70%, at least 80%, at least 90%, at least 95%, at least 96%, at least 97%, at least 98%, at least 99%.

The *Bacillus stearothermophilus* alpha-amylase variant may be a variant of the one shown in SEQ ID NO: 1 or may be one having sequence identity thereto of at least 60%, at least 70%, at least 80%, at least 90%, at least 95%, at least 96%, at least 97%, at least 98%, at least 99%, but less than 100%.

In an embodiment the *Bacillus stearothermophilus* alpha-amylase variant has from 1-12 mutations, such as 1, 2, 3, 4, 5, 6, 7, 8, 9, 10, 11, or 12 mutations, compared to the parent alpha-amylase, especially the parent alpha-amylase shown in SEQ ID NO: 1.

In an embodiment the pH in step (a) is from 4-7, preferably 4.5-6.

Step (a) is followed by saccharification of dextrins in step (b). However, a process of the invention may further comprise a pre-saccharification step, i.e., after step (a), but before saccharification step (b), carried out for 40-90 minutes at a temperature between 30-65° C.

When step (a) is carried out at a temperature above the initial gelatinization temperature a jet-cooking step may be carried out before in step (a). Jet-cooking may be carried out at a temperature between 95-140° C. for about 1-15 minutes, preferably for about 3-10 minutes, especially around about 5 minutes.

In a preferred embodiment a process of the invention further comprises, before step (a), the steps of:
i) reducing the particle size of the starch-containing material, preferably by dry milling;
ii) forming a slurry comprising the starch-containing material and water.

In an embodiment the process of recovering oil of the invention comprises
(a) converting a starch-containing material into dextrins with an alpha-amylase at a temperature below the initial gelatinization temperature;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease and a phospholipase are present and/or added during steps (a) to (c).

In a preferred embodiment the saccharification step (b) and fermentation step (c) are carried out simultaneously, preferably at a temperature below the initial gelatinization temperature, or sequentially.

In an embodiment steps (a), (b), and (c) are carried out simultaneously. This is typically done at a temperature below the initial gelatinization temperature, i.e. raw starch hydrolysis process (RSH). However, steps (a), (b), and (c) may also be carried out sequentially at temperatures below the initial gelatinization temperature, such as between 20-60° C., preferably between 25-40° C., such as around 32° C.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein. S. and Lii. C, Starch/Starke, Vol. 44 (12) pp. 461-466 (1992).

According to the invention saccharification step (b) may be carried out at a temperature from 20-75° C., preferably from 40-70° C., such as around 60° C., and at a pH between 4 and 5.

In a preferred embodiment fermentation step (c) or simultaneous saccharification and fermentation (SSF) (i.e., combined steps (b) and (c)) are carried out carried out at a temperature between 20-60° C., preferably between 25-40° C., such as around 32° C. In an embodiment fermentation step (c) or simultaneous saccharification and fermentation (SSF) (i.e., combined steps (b) and (c)) are ongoing for 6 to 120 hours, in particular 24 to 96 hours. In an embodiment the starch-containing material converting step (a), saccharification step (b) and fermentation step (c) are carried out simultaneously or sequentially.

In an embodiment the starch-containing material converting step (a) is carried out at a temperature below the initial gelatinization temperature, preferably from 20-60° C., preferably between 25-40° C., such as around 28-36° C., such as around 32° C. In an embodiment the starch-containing material is converted to dextrins and the dextrins are saccharified to a sugar by treating the starch-containing material with an alpha-amylase and carbohydrate-source generating enzyme, in particular a glucoamylase, below the initial gelatinization temperature of the starch-containing material. In an embodiment the conversion of the starch-containing material to dextrins, the saccharification of the dextrins to sugars, and the fermentation of the sugars are carried out in a single step (i.e., raw starch hydrolysis step).

When the process of the invention is carried out as a raw starch hydrolysis process (i.e., single step process or no-cook process) the glucoamylase may preferably be derived from a strain of *Trametes*, such as a strain of *Trametes cingulata*, or a strain of *Athelia*, such as a strain of *Athelia rolfsii*. Preferred alpha-amylases used in a raw starch hydrolysis process include alpha-amylases derived from a strain *Rhizomucor*, such as a strain of *Rhizomucor pusillus*, such as a *Rhizomucor pusillus* alpha-amylase with a starch-binding domain (SBD), such as a *Rhizomucor pusillus* alpha-amylase with *Aspergillus niger* glucoamylase linker and SBD. Generally the starch-containing material in raw starch hydrolysis processes (i.e., no-cook processes) are granular starch. Said granular starch may be reduced the particle size, preferably by milling, to from 0.05 to 3.0 mm, preferably 0.1-0.5 mm.

Also the sugar level, such as glucose level, may be kept below 6 wt.-%, preferably below about 3 wt.-%, preferably below about 2 wt.-%, more preferred below about 1 wt.-%., even more preferred below about 0.5%, or even more preferred 0.25% wt.-%, such as below about 0.1 wt.-%. The pH may be from 4-7, preferably 4.5-6.0, when conversion of the starch-containing material to dextrins, the saccharification of the dextrins to a sugar, and the fermentation of the sugar are carried out in a single step. If the process of the invention is carried out as a conventional process (i.e., step (a) is carried out as a liquefaction step at a temperature above the gelatinization temperature) the carbohydrate-source generating enzyme used in step (b) is preferably a glucoamylase derived from *Aspergillus*, preferably *A. niger*, *A. awamori*, or *A. oryzae*; or a strain of *Trichoderma*, preferably *Trichoderma reesei*; or a strain of *Talaromyces*, preferably *Talaromyces emersonii*, or a strain of *Pycnoporus*, or a strain of *Gloeophyllum*.

Examples of other suitable glucoamylase can be found below in the "Glucoamylases" section below.

Generally the starch-containing material in step (a), including granular starch, contains 20-55 wt.-% dry solids, preferably 25-40 wt.-% dry solids, more preferably 30-35% dry solids. Separation (i.e. dewatering) in step (e) may be carried out by centrifugation, preferably a decanter centrifuge, filtration, preferably using a filter press, a screw press, a plate-and-frame press, a gravity thickener or decker or any other separation technology known in the art.

The (desired) fermentation product may in an embodiment be selected from the group consisting of alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, B12, beta-carotene); and hormones. In a preferred embodiment the (desired) fermentation product is ethanol. According to the invention the desired fermentation product may be recovered by distillation. According to the invention oil may be recovered from the thin stillage and/or syrup/evaporated centrate, e.g., by extraction, such as hexane extraction.

Separating (Dewatering) Whole Stillage into Thin Stillage and Wet Cake in Step (e)

Separating whole stillage into thin stillage and wet cake in step (e), in order to remove a significant portion of the liquid/water, may be done using any suitable separation technique, including centrifugation, pressing and filtration. In a preferred embodiment the separation/dewatering is carried out by centrifugation. Preferred centrifuges in industry are decanter type centrifuges, preferably high speed decanter type centrifuges. An example of a suitable centrifuge is the NX 400 steep cone series from Alfa Laval which is a high-performance decanter. In another preferred embodiment the separation is carried out using other conventional separation equipment such as a plate/frame filter presses, belt filter presses, screw presses, gravity thickeners and deckers, or similar equipment.

Drying of Wet Cake

After the wet cake, containing about 30-35 wt-% dry solids, has been separated from the thin stillage (e.g., dewatered) it may be dried in a drum dryer, spray dryer, ring drier, fluid bed drier or the like in order to produce "Distillers Dried Grains" (DDG). DDG is a valuable feed ingredient for livestock, poultry and fish. It is preferred to provide DDG with a content of less than about 10-12 wt.-% moisture to avoid mold and microbial breakdown and increase the shelf life. Further, high moisture content also makes it more expensive to transport DDG. The wet cake is preferably dried under conditions that do not denature proteins in the wet cake. The wet cake may be blended with syrup separated from the thin stillage and dried into DDG with Solubles (DDGS).

Fermenting Organisms

Examples of fermenting organisms used in step c) for fermenting sugars in a fermentation medium into a desired fermentation product include fungal organisms, such as especially yeast. Preferred yeast includes strains of *Saccharomyces* spp., in particular, *Saccharomyces cerevisiae*.

In one embodiment the fermenting organism is added to the fermentation medium, so that the viable fermenting organism, such as yeast, count per mL of fermentation medium is in the range from $10^5$ to $10^{12}$, preferably from $10^7$ to $10^{10}$, especially about $5 \times 10^7$.

Commercially available yeast includes, e.g., RED STAR™ and ETHANOL RED yeast (available from Fermentis/Lesaffre, USA), FALI (available from Fleischmann's Yeast, USA), SUPERSTART and THERMOSACC™ fresh yeast (available from Ethanol Technology, Wis., USA), BIOFERM AFT and XR (available from NABC—North American Bioproducts Corporation, Ga., USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived there from, or cereals. Contemplated are also waxy and non-waxy types of corn and barley.

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes. The fermentation product, such as ethanol, obtained according to the invention, may be used as fuel which may be blended with gasoline. However, in the case of ethanol it may also be used as potable ethanol.

Recovery

Subsequent to fermentation the fermentation product, such as ethanol, may be separated from the fermentation medium, e.g., by distillation. Alternatively the desired fermentation product may be extracted from the fermentation medium by micro or membrane filtration techniques. The fermentation product may also be recovered by stripping or other method well known in the art.

Use of Protease and Phospholipase for Improving Oil Extraction

In an aspect, the invention relates to the use of a protease in combination with a phospholipase for increasing oil recovery yields from thin stillage and/or syrup in a fermentation product production process. FIG. 1 shows a typical fermentation product production process including where oil extraction typically is done.

Enzymes

One or more of the following enzyme activities may be used according to the invention.

Alpha-Amylases

The process of the invention, including step (a), may be carried out using a suitable alpha-amylase. In a preferably embodiment a bacterial alpha-amylase and/or a fungal alpha-amylase may be used.

The alpha-amylase may be bacterial when step (a) is carried out as a liquefaction step at high temperatures, i.e., above the initial gelatinization temperature.

The alpha-amylase may be fungal when step (a) is carried out at a temperature below the initial gelatinization temperature, such as when steps (a), (b) and (c) are carried out as a raw starch hydrolysis (single step process or no-cook process) as described above.

Bacterial Alpha-Amylases

Examples of suitable bacterial alpha-amylases include the below mentioned. Preferred bacterial alpha-amylases used in step i) may be derived from a strain the genus *Bacillus* (sometimes referred to as *GeoBacillus*), including a strain of *Bacillus licheniformis, Bacillus amyloliquefaciens, Bacillus stearothermophilus*, or *Bacillus subtilis*. Other bacterial alpha-amylases include alpha-amylase derived from a strain of the *Bacillus* sp. NCIB 12289, NCIB 12512, NCIB 12513 or DSM 9375, all of which are described in detail in WO 95/26397, and the alpha-amylase described by Tsukamoto et al., Biochemical and Biophysical Research Communications, 151 (1988), pp. 25-31 (hereby incorporated by reference).

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or U.S. Pat. No. 6,187,576 (hereby incorporated by reference) and include *Bacillus stearothermophilus* alpha-amylase (BSG alpha-amylase) variants having a deletion of one or two amino acid in positions R179 to G182, preferably a double deletion disclosed in WO 1996/023873—see e.g., page 20, lines 1-10 (hereby incorporated by reference), preferably corresponding to delta(181-182) compared to the wild-type BSG alpha-amylase amino acid sequence set forth in SEQ ID NO:3 disclosed in WO 99/19467 or SEQ ID NO: 1 herein, or deletion of amino acids R179+G180 using SEQ ID NO:3 in WO 99/19467 or SEQ ID NO: 1 herein for numbering (which reference is hereby incorporated by reference). Even more preferred are *Bacillus* alpha-amylases, especially *Bacillus stearothermophilus* alpha-amylase, which have a double deletion corresponding to delta(181-182) and optionally further comprising a N193F substitution (also denoted I181*+G182*+N193F) compared to the wild-type BSG alpha-amylase amino acid sequence set forth in SEQ ID NO:3 disclosed in WO 99/19467 or SEQ ID NO: 1 herein.

In an embodiment the *Bacillus stearothermophilus* alpha-amylase is one disclosed in WO 2011/082425, such as one selected from the group of:
I181*+G182*;
I181*+G182*+N193F;
preferably
I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A+Q89R+E129V+K177L+R179E+Q254S+M284V; and
I181*+G182*+N193F+E129V+K177L+R179E+K220P+N224L+S242Q+Q254S (using SEQ ID NO: 1 herein for numbering).

In an embodiment the *Bacillus stearothermophilus* alpha-amylase has the following mutations: I81*+G182*+N193F+V59A+Q89R+E129V+K177L+R179E+Q254S+M284V (SEQ ID NO: 1).

The truncated *Bacillus stearothermophilus* alpha-amylase is typically naturally truncated to be about 491 amino acids long, such as from 485-495 amino acids long.

A hybrid alpha-amylase specifically contemplated comprises 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with the following substitution: G48A+T49I+G107A+H156Y+A181T+N190F+I201F+A209V+Q264S (using the numbering in SEQ ID NO: 4 in WO 99/19467). Especially preferred are variants having one or more of the mutations H154Y, A181T, N190F, A209V and Q264S and/or deletion of two residues between positions 176 and 179, preferably deletion of E178 and G179 (using the SEQ ID NO: 5 numbering of WO 99/19467).

Commercially available bacterial alpha-amylase products and products containing alpha-amylases include TERMAMYL™ SC, LIQUOZYME™ SC, LIQUOZYME™ LpH, AVANTEC™, AVANTEC™ AMP, BAN (Novozymes A/S, Denmark) DEX-LO™, SPEZYME™ XTRA, SPEZYME™ AA, SPEZYME FRED-L, SPEZYME™ ALPHA, GC358, SPEZYME RSL, SPEZYME HPA and SPEZYME™ DELTA AA (from DuPont, USA), FUELZYME™ (Verenium, USA).

A bacterial alpha-amylase may be added in step (a) in amounts as are well-known in the art. When measured in KNU units (described below in the "Materials & Methods"-section) the alpha-amylase activity is preferably present in an amount of 0.5-5,000 NU/g of DS, in an amount of 1-500 NU/g of DS, or more preferably in an amount of 5-1,000 NU/g of DS, such as 10-100 NU/g DS.

Fungal Alpha-Amylases

Fungal alpha-amylases (EC 3.2.1.1) are preferably of filamentous fungus origin. The fungal alpha-amylase may be a fungal acid alpha-amylase.

Fungal acid alpha-amylases include acid alpha-amylases derived from a strain of the genus *Aspergillus*, such as *Aspergillus oryzae* and *Aspergillus niger* alpha-amylases.

A preferred fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e. more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from *Aspergillus niger* is SP288 (available from Novozymes A/S, Denmark).

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid fungal alpha-amylase is derived from a strain of *Aspergillus kawachii*.

Commercial available compositions comprising fungal alpha-amylase include FUNGAMYL™ and the acid fungal alpha-amylase sold under the trade name SP288 (available from Novozymes A/S, Denmark).

In an embodiment the fungal acid alpha-amylase is a hybrid alpha-amylase. Preferred examples of fungal hybrid alpha-amylases include the ones disclosed in WO 2005/003311 or U.S. Patent Publication no. 2005/0054071 (Novozymes) or U.S. patent application No. 60/638,614 (Novozymes) which is hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Table 1 to 5 of the examples in U.S. patent application No. 60/638,614, including Fungamyl variant with catalytic domain JA1 18 and *Athelia rolfsii* SBD and SEQ ID NO: 100 in U.S. 60/638,614), *Rhizomucor pusillus* alpha-amylase with *Athelia rolfsii* AMG linker and SBD (SEQ ID NO:101 in U.S. 60/638,614), *Rhizomucor pusillus* alpha-amylase with *Aspergillus niger* glucoamylase linker and SBD (which is disclosed in Table 5 as a combination of amino acid sequences SEQ ID NO:20, SEQ ID NO:72 and SEQ ID NO:96 in U.S. application Ser. No. 11/316,535), and *Meripilus giganteus* alpha-amylase with *Athelia rolfsii* glucoamylase linker and SBD (SEQ ID NO:102 in U.S. 60/638,614). Other specifically contemplated hybrid alpha-amylases are any of the ones listed in Tables 3, 4, 5, and 6 in Example 4 in U.S. application Ser. No. 11/316,535 or WO 2006/069290 (hereby incorporated by reference). Other specific examples of contemplated hybrid alpha-amylases include those disclosed in U.S. Patent Publication no. 2005/0054071, including those disclosed in Table 3 on page 15, such as *Aspergillus niger* alpha-amylase with *Aspergillus kawachii* linker and starch binding domain.

In a preferred embodiment the alpha-amylase is one disclosed in WO 2013/006756 including the following variants: *Rhizomucor pusillus* alpha-amylase variant having an *Aspergillus niger* glucoamylase linker and starch-binding domain (SBD) which further comprises at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 2 in WO 2013/006756 for numbering) (all incorporated by reference).

An acid alpha-amylases may according to the invention be added in an amount of 0.1 to 10 AFAU/g DS, preferably 0.10 to 5 AFAU/g DS, especially 0.3 to 2 AFAU/g DS.

Fungal alpha-amylases may be added to step (a) in a well know effective amount, preferably in the range from 0.001-1 mg enzyme protein per g DS, preferably 0.01-0.5 mg enzyme protein per g DS.

Carbohydrate-Source Generating Enzyme

According to the invention a carbohydrate-source generating enzyme, preferably a glucoamylase, is present in step (b), and may be present and/or added during step (a), saccharification step (b) and/or fermentation step (c) or simultaneous saccharification step (b) and fermentation step (c) (SSF).

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used.

Specific examples include glucoamylase (being glucose generators), beta-amylase and maltogenic amylase (being maltose generators).

In a preferred embodiment the carbohydrate-source generating enzyme is a glucoamylase.

Glucoamylases

The process of the invention, including steps (b) and/or (c), may be carried out using any suitable glucoamylase. In a preferably embodiment the glucoamylase is of bacterial or fungal origin.

Contemplated glucoamylases include those from the group consisting of *Aspergillus* glucoamylases, in particular *A. niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *A. oryzae* glucoamylase (AgriC. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1 199-1204.

Other glucoamylases contemplated include glucoamylase derived from a strain of *Athelia*, preferably a strain of *Athelia rolfsii* (previously denoted *Corticium rolfsii*) glucoamylase (see U.S. Pat. No. 4,727,026 and (Nagasaka, Y. et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). Also contemplated are the *Trichoderma reesei* glucoamylases disclosed as SEQ ID NO: 4 in WO 2006/060062 and glucoamylases being at least 80% or at least 90% identical thereto and further the glucoamylase derived from *Humicola grisea* disclosed as SEQ ID NO: 3 in U.S. Ser. No. 10/992,187 (hereby incorporated by reference) or sequences having at least 80% or at least 90% identity thereto.

In a preferred embodiment the glucoamylase is derived from a strain of *Aspergillus*, preferably *A. niger, A. awamori*, or *A. oryzae*; or a strain of *Trichoderma*, preferably *T reesei*; or a strain of *Talaromyces*, preferably *T emersonii*.

In an embodiment the glucoamylase present and/or added during saccharification step (b) and/or fermentation step (c) is of fungal origin, preferably from a strain of *Pycnoporus*, or a strain of *Gloeophyllum*. In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576 or SEQ ID NO: 13 herein.

In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 12 herein.

Other contemplated glucoamylases include glucoamylase derived from a strain of *Trametes*, preferably a strain of *Trametes cingulata* disclosed in WO 2006/069289 (which is hereby incorporated by reference). Also hybrid glucoamylase are contemplated according to the invention. Examples the hybrid glucoamylases disclosed in WO 2005/045018. Specific examples include the hybrid glucoamylase disclosed in Table 1 and 4 of Example 1 (which hybrids are hereby incorporated by reference).

Bacterial glucoamylases contemplated include glucoamylases from the genus *Clostridium*, in particular *C. thermoamylolyticum* (EP 135,138), and *C. thermohydrosulfuricum* (WO 86/01831).

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ ULTRA, SPIRIZYME™ EXCEL, SPIRIZYME™ ACHIEVE, SPIRIZYME™ B4U and AMG™ E (from Novozymes A/S); OPTIDEX™ 300 (from Genencor Int.); AMIGASE™ and AMIGASE™ PLUS (from DSM); G-ZYME™ G900, G-ZYME™ and G990 ZR (from Genencor Int.).

Glucoamylases may in an embodiment be added in an amount of 0.02-20 AGU/g DS, preferably 0.05-5 AGU/g DS (in whole stillage), especially between 0.1-2 AGU/g DS.

Glucoamylase may be added in an effective amount, preferably in the range from 0.001-1 mg enzyme protein per g DS, preferably 0.01-0.5 mg enzyme protein per g dry solid (DS).

Phospholipases

Phospholipases act to hydrolyse phospholipids into their constituent fatty acids and lipophilic moieties. A preferred type of phospholipase is phospholipase C. Suitable phospholipases for use in the invention are derived from organisms, preferably from bacteria or fungi. Preferred phospholipases are derived from *Kionochaeata* sp. (e.g., SEQ ID NO: 15), *Penicillium emersonii* (e.g., SEQ ID NO: 16) and *Bacillus thuringensis* (e.g., SEQ ID NO: 17), with phospholipase from *Penicillium emersonii* being preferred.

The invention is further summarized in the following paragraphs:

1. A process of recovering oil, comprising
(a) converting a starch-containing material into dextrins with an alpha-amylase;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease and a phospholipase are present and/or added during steps (a) to (c).

2. The process of paragraph 1, preferably wherein the protease and the phospholipase are present and/or added during steps (b) and/or (c).

3. The process of paragraph 1 or 2, wherein the protease present and/or added in steps (a) to (c), preferably steps (b) and/or (c), is a protease (e.g., derived from *Meripilus giganteus*) having the amino acid sequence set out in SEQ ID NO: 14 herein, or is a protease which has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 14 herein.

4. The process of paragraph 1 or 2, wherein the protease present and/or added in steps (a) to (c), preferably (b) and/or (c), is a protease (e.g., derived from *Thermoascus aurantiacus*) having the amino acid sequence set out in SEQ ID NO: 3 herein, or is a protease which has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 3 herein.

5. The process of any of paragraphs 1-4 wherein the phospholipase, present and/or added in steps (a) to (c), preferably steps (b) and/or (c), is a phospholipase C.

6. The process of any of paragraphs 1-5, wherein the phospholipase, present and/or added in steps (a) to (c), preferably steps (b) and/or (c), has the amino acid sequence of SEQ ID NO: 15 herein; SEQ ID NO: 16 herein; or SEQ ID NO: 17 herein, preferably where the phospholipase has the amino acid sequence of SEQ ID NO: 16 herein.

7. The process of any of paragraphs 1-5, wherein the phospholipase, present and/or added in steps (a) to (c), preferably steps (b) and/or (c), is derived from *Kionochaeta*, such as the phospholipase shown in SEQ ID NO: 15 herein or one having a sequence identity thereto of at least 60%, at least 70%, at least 80%, at least 90%, at least 95%, at least 96%, at least 97%, at least 98%, at least 99%.

8. The process of any of paragraphs 1-5, wherein the phospholipase, present and/or added in steps (a) to (c), preferably steps (b) and/or (c), is derived from *Penicillium*, such as the phospholipase shown in SEQ ID NO: 16 herein or one having a sequence identity thereto of at least 60%, at least 70%, at least 80%, at least 90%, at least 95%, at least 96%, at least 97%, at least 98%, at least 99%.

9. The process of any of paragraphs 1-5, wherein the phospholipase, present and/or added in steps (a) to (c), preferably steps (b) and/or (c), is derived from *Bacillus*, such as the phospholipase shown in SEQ ID NO: 17 herein or one having a sequence identity thereto of at least 60%, at least 70%, at least 80%, at least 90%, at least 95%, at least 96%, at least 97%, at least 98%, at least 99%.

10. The process of any of paragraphs 1-9, wherein the protease and the phospholipase are added sequentially or simultaneously.

11. The process of recovering oil of any of paragraphs 1-10, comprising
(a) converting a starch-containing material into dextrins with an alpha-amylase at a temperature above the initial gelatinization temperature;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease and a phospholipase are present and/or added during steps (b) and/or (c).

12. The process of paragraphs 1-11, wherein the temperature in step (a) is above the initial gelatinization temperature, such as at a temperature between 80-90° C., such as around 85° C.

13. The process of any of paragraphs 11-12, wherein a protease derived from a strain of *Pyrococcus*, preferably a strain of *Pyrococcus furiosus*, is added in step (a) carried out above the initial gelatinization temperature.

14. The process of paragraphs 11-13, wherein the protease is the one shown SEQ ID NO: 4 herein, or wherein the protease has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 4 herein.

15. The process of any of paragraphs 11-14, wherein the protease, added in step (a) carried out at a temperature above the initial gelatinization temperature, has a thermostability of more than 20%, more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

16. The process of any of paragraphs 11-15, wherein the protease, added in step (a) carried out at a temperature above the initial gelatinization temperature, has a thermostability between 50 and 115%, such as between 50 and 70%, such as between 50 and 60%, such as between 100 and 120%, such as between 105 and 115% determined as Relative Activity at 80° C./70° C.

17. The process of any of paragraphs 11-16, wherein the protease, added in step (a) carried out at a temperature above the initial gelatinization temperature, has a thermostability of more than 12%, more than 14%, more than 16%, more than 18%, more than 20%, more than 25%, more than 30%, more than 40%, more that 50%, more than 60%, more than 70%, more than 80%, more than 90%, more than 100%, more than 110% determined as Relative Activity at 85° C./70° C.

18. The process of any of paragraphs 11-17, wherein the bacterial alpha-amylase is derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein, in particular the *Bacillus stearothermophilus* alpha-amylase is truncated, preferably to have from 485-495 amino acids, such as around 491 amino acids.

19. The process of recovering oil of paragraphs 1-10, comprising
(a) converting a starch-containing material into dextrins with an alpha-amylase at a temperature below the initial gelatinization temperature;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease and a phospholipase are present and/or added during steps (a) to (c).

20. The process of paragraph 19, wherein saccharification step (b) and fermentation step (c) are carried out simultaneously, preferably at a temperature below the initial gelatinization temperature, or sequentially.

21. The process of paragraph 19, wherein steps (a), (b) and (c) are carried out simultaneously or sequentially at a temperature below the initial gelatinization temperature.

22. Use of a protease and a phospholipase for increasing oil recovery yields from thin stillage and/or syrup in a fermentation product production process.

23. The use of paragraph 22, wherein the protease (e.g., derived from *Meripilus giganteus*) has the amino acid sequence set out in SEQ ID NO: 14 herein, or is a protease which has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 14 herein.

24. The use of paragraph 22, wherein the protease (e.g., derived from *Thermoascus aurantiacus*) having the amino acid sequence set out in SEQ ID NO: 3 herein, or is a protease which has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 3 herein.

25. The use of any of paragraphs 22-24, wherein the phospholipase is a phospholipase C.

26. The use of any of paragraphs 22-25, wherein the phospholipase has the amino acid sequence of SEQ ID NO: 15 herein; SEQ ID NO: 16 herein; or SEQ ID NO: 17 herein, preferably where the phospholipase has the amino acid sequence of SEQ ID NO: 16 herein.

27. The use of any of paragraphs 22-26, wherein the phospholipase is derived from *Kionochaeta*, such as the phospholipase shown in SEQ ID NO: 15 herein or one having a sequence identity thereto of at least 60%, at least 70%, at least 80%, at least 90%, at least 95%, at least 96%, at least 97%, at least 98%, at least 99%.

28. The use of any of paragraphs 22-26, wherein the phospholipase is derived from *Penicillium*, such as the phospholipase shown in SEQ ID NO: 16 herein or one having a sequence identity thereto of at least 60%, at least 70%, at least 80%, at least 90%, at least 95%, at least 96%, at least 97%, at least 98%, at least 99%.

29. The use of any of paragraphs 22-26, wherein the phospholipase is derived from *Bacillus*, such as the phospholipase shown in SEQ ID NO: 17 herein or one having a sequence identity thereto of at least 60%, at least 70%, at least 80%, at least 90%, at least 95%, at least 96%, at least 97%, at least 98%, at least 99%.

30. The use of any of paragraphs 22-29, wherein the protease and the phospholipase are added sequentially or simultaneously.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties. The present invention is further described by the following examples which should not be construed as limiting the scope of the invention.

Material & Methods

Enzymes: Alpha-Amylase LSCDS ("LSCDS"): *Bacillus stearothermophilus* alpha-amylase with the mutations: I181*+G182*+N193F truncated to be around 491 amino acids long (SEQ ID NO: 1 herein).

Alpha-Amylase 369: (AA369): *Bacillus stearothermophilus* alpha-amylase with the mutations: I181*+G182*+N193F+V59A+Q89R+E129V+K177L+R179E+Q254S+M284V truncated to be around 491 amino acids long (SEQ ID NO: 1 herein).

Protease OX ("OX"): Metallo protease derived from *Thermoascus aurantiacus* CGMCC No. 0670 disclosed as amino acids 1-177 in SEQ ID NO: 3 herein Protease PF ("PF"): Protease derived from the bacterium *Pyrococcus furiosus* shown in SEQ ID NO: 4 herein.

Protease RH ("RH"): Protease derived from a filamentous fungus *Rhizomucor miehei* shown in SEQ ID NO: 9 herein.

Protease TF ("TF"): Protease derived from a filamentous fungus *Thermobifida fusca* shown in SEQ ID NO: 10 herein.

Determination of Alpha-Amylase Activity

1. Phadebas™ Assay

Alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units. In this absorbance range there is linearity between activity and absorbance (Lambert-Beer law). The dilution of the enzyme must therefore be adjusted to fit this criterion. Under a specified set of conditions (temperature, pH, reaction time, buffer conditions) 1 mg of a given alpha-amylase will hydrolyze a certain amount of substrate and a blue colour will be produced. The measured absorbance is directly proportional to the specific activity (activity/mg of pure alpha-amylase protein) of the alpha-amylase in question under the given set of conditions.

2. Alternative Method

Alpha-amylase activity is alternatively determined by a method employing the PNP-G7 substrate. PNP-G7 which is an abbreviation for p-nitrophenyl-alpha,D-maltoheptaoside, which is a blocked oligosaccharide that can be cleaved by an endo-amylase. Following the cleavage, the alpha-glucosidase included in the kit digest the substrate to liberate a free PNP molecule which has a yellow colour and thus can be measured by visible spectophometry at wavelength Lambda=405 nm (400-420 nm). Kits containing PNP-G7 substrate and alpha-glucosidase are manufactured by Bohringer-Mannheim (cat. No. 1054635).

To prepare the substrate one bottle of substrate (BM 1442309) is added to 5 ml buffer (BM1442309). To prepare the alpha-glucosidase one bottle of alpha-glucosidase (BM 1462309) is added to 45 ml buffer (BM1442309). The working solution is made by mixing 5 ml alpha-glucosidase solution with 0.5 ml substrate.

The assay is performed by transforming 20 microL enzyme solution to a 96 well microtitre plate and incubating at 25° C. 200 microL working solution, 25° C. is added. The solution is mixed and pre-incubated 1 minute and absorption is measured every 15 seconds over 3 minutes at OD 405 nm.

The slope of the time dependent absorption-curve is directly proportional to the specific activity (activity per mg enzyme) of the alpha-amylase in question under the given set of conditions.

Determination of Acid Amylolytic Activity (FAU)

One Fungal Alpha-Amylase Unit (1 FAU) is defined as the amount of enzyme, which breaks down 5.26 g starch (Merck Amylum solubile Erg. B.6, Batch 9947275) per hour at Novozymes' standard method for determination of alpha-amylase based upon the following standard conditions:

| | |
|---|---|
| Substrate | Soluble starch |
| Temperature | 37° C. |
| pH | 4.7 |
| Reaction time | 7-20 minutes |

A detailed description of Novozymes' method for determining KNU and FAU is available on request as standard method EB-SM-0009.02/01. Determination of acid alpha-amylase activity (AFAU)

Acid alpha-amylase activity is measured in AFAU (Acid Fungal Alpha-amylase Units), which are determined relative to an enzyme standard.

The standard used is AMG 300 L (wild type *A. niger* G1 AMG sold by Novozymes A/S). The neutral alpha-amylase in this AMG falls after storage at room temperature for 3 weeks from approx. 1 FAU/mL to below 0.05 FAU/mL.

The acid alpha-amylase activity in this AMG standard is determined in accordance with AF 9 1/3 (Novo method for the determination of fungal alpha-amylase). In this method, 1 AFAU is defined as the amount of enzyme, which degrades 5.260 mg starch dry matter per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

Alpha-amylase Starch+Iodine→Destrins+Oligosaccharides 40° C., pH 2.5 Blue/violet *t*=23 sec. Decolouration Standard Conditions/Reaction Conditions: (Per Minute)
Substrate: starch, approx. 0.17 g/L
Buffer: Citrate, approx. 0.03 M
Iodine ($I_2$): 0.03 g/L
$CaCl_2$: 1.85 mM
pH: 2.50±0.05
Incubation temperature: 40° C.
Reaction time: 23 seconds
Wavelength: Lambda=590 nm
Enzyme concentration: 0.025 AFAU/mL
Enzyme working range: 0.01-0.04 AFAU/mL Further details can be found in standard method document EB-SM-0259.02/01 available on request from Novozymes A/S, which folder is hereby incorporated by reference.

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum soluble.

A folder EB-SM-0009.02/01 describing this analytical method in more detail is available upon request to Novozymes A S, Denmark, which folder is hereby included by reference.

Glucoamylase and Alpha-Glucosidase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

AMG Incubation:

| | |
|---|---|
| Substrate: | maltose 23.2 mM |
| Buffer: acetate | 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

Color Reaction:

| | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Determination of Protease Activity (AU)

Dimethyl casein (DMC) is hydrolyzed by the proteolytic enzyme to small peptides. The primary amino groups formed in this process react with trinitrobenzene sulphonic acid (TNBS) forming a coloured complex. This colour development is monitored in situ so the change in absorption per time unit can be calculated. This FIGURE is a measure of the reaction rate and thus of the enzyme activity.

| Reaction conditions for the DMC reaction | |
|---|---|
| Temperature: | 50° C. |
| pH: | 8.3 |
| Wavelength: | 405 nm |
| Reaction time: | 8 min. |

-continued

| Reaction conditions for the DMC reaction | |
|---|---|
| Measuring time: | 2 min. |
| Enzyme concentration range: | 0.072-0.216 mAU/ml. |

The activity is determined relative to an enzyme standard.

The assay is further described in standard method document EB-SM-0218.02/02 available upon request from Novozymes A/S, Denmark.

EXAMPLES

Example 1

Preparation of Protease Variants and Test of Thermostability

Chemicals used were commercial products of at least reagent grade.

Strains and Plasmids:

E. coli DH12S (available from Gibco BRL) was used for yeast plasmid rescue. pJTPOO is a S. cerevisiae and E. coli shuttle vector under the control of TPI promoter, constructed from pJC039 described in WO 01/92502, in which the Thermoascus aurantiacus M35 protease gene (WO 03/048353) has been inserted.

Saccharomyces cerevisiae YNG318 competent cells: MATa Dpep4[cir+] ura3-52, leu2-D2, his 4-539 was used for protease variants expression. It is described in J. Biol. Chem. 272(15): 9720-9727 (1997).

Media and Substrates

10× Basal solution: Yeast nitrogen base w/o amino acids (DIFCO) 66.8 g/L, succinate 100 g/l, NaOH 60 g/l.

SC-glucose: 20% glucose (i.e., a final concentration of 2%=2 g/100 mL)) 100 mL/L, 5% threonine 4 mL/L, 1% tryptophan 10 ml/1, 20% casamino acids 25 ml/1, 10× basal solution 100 ml/1. The solution is sterilized using a filter of a pore size of 0.20 micrometer. Agar (2%) and $H_2O$ (approx. 761 mL) is autoclaved together, and the separately sterilized SC-glucose solution is added to the agar solution.

YPD: Bacto peptone 20 g/l, yeast extract 10 g/L, 20% glucose 100 mL/L.

YPD+Zn: YPD+0.25 mM ZnSO4.

PEG/LiAc solution: 40% PEG4000 50 ml, 5 M Lithium Acetate 1 mL.

96 well Zein micro titre plate:

Each well contains 200 microL of 0.05-0.1% of zein (Sigma), 0.25 mM $ZnSO_4$ and 1% of agar in 20 mM sodium acetate buffer, pH 4.5.

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, N.Y.; Ausubel, F. M. et al. (eds.) "Current protocols in Molecular Biology", John Wiley and Sons, 1995; Harwood, C. R. and Cutting, S. M. (Eds.).

Yeast Transformation

Yeast transformation was performed using the lithium acetate method. 0.5 microL of vector (digested by restriction endnucleases) and 1 microL of PCR fragments is mixed. The DNA mixture, 100 microL of YNG318 competent cells, and 10 microL of YEAST MAKER carrier DNA (Clontech) is added to a 12 mL polypropylene tube (Falcon 2059). Add 0.6 mL PEG/LiAc solution and mix gently. Incubate for 30 min at 30° C., and 200 rpm followed by 30 min at 42° C. (heat shock). Transfer to an eppendorf tube and centrifuge for 5 sec. Remove the supernatant and resolve in 3 mL of YPD. Incubate the cell suspension for 45 min at 200 rpm at 30° C. Pour the suspension to SC-glucose plates and incubate 30° C. for 3 days to grow colonies. Yeast total DNA are extracted by Zymoprep Yeast Plasmid Miniprep Kit (ZYMO research).

DNA Sequencing

E. coli transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Construction of Protease Expression Vector

The Themoascus M35 protease gene was amplified with the primer pair Prot F (SEQ ID NO: 5) and Prot R (SEQ ID NO: 6). The resulting PCR fragments were introduced into S. cerevisiae YNG318 together with the pJC039 vector (described in WO 2001/92502) digested with restriction enzymes to remove the Humicola insolens cutinase gene. The Plasmid in yeast clones on SC-glucose plates was recovered to confirm the internal sequence and termed as pJTPOOL Construction of Yeast Library and Site-Directed Variants Library in yeast and site-directed variants were constructed by SOE PCR method (Splicing by Overlap Extension, see "PCR: A practical approach", p. 207-209, Oxford University press, eds. McPherson, Quirke, Taylor), followed by yeast in vivo recombination.

General Primers for Amplification and Sequencing

The primers AM34 (SEQ ID NO: 7) and AM35 (SEQ ID NO:8) were used to make DNA fragments containing any mutated fragments by the SOE method together with degenerated primers (AM34+Reverse primer and AM35+forward primer) or just to amplify a whole protease gene (AM34+AM35).

| PCR reaction system: | | Conditions: |
|---|---|---|
| 48.5 microL $H_2O$ | 1 | 94° C. 2 min |
| 2 beads puRe Taq Ready-To-Go PCR (Amersham Biosciences) | 2 | 94° C. 30 sec |
| 0.5 microL × 2 100 pmole/microL of primers | 3 | 55° C. 30 sec |
| 0.5 microL template DNA | 4 | 72° C. 90 sec |
| | 2-4 | 25 cycles |
| | 5 | 72° C. 10 min |

DNA fragments were recovered from agarose gel by the Qiagen gel extraction Kit. The resulting purified fragments were mixed with the vector digest. The mixed solution was introduced into Saccharomyces cerevisiae to construct libraries or site-directed variants by in vivo recombination.

Relative Activity Assay

Yeast clones on SC-glucose were inoculated to a well of a 96-well micro titre plate containing YPD+Zn medium and cultivated at 28° C. for 3 days. The culture supernatants were applied to a 96-well zein micro titer plate and incubated at at least 2 temperatures (ex., 70° C. and 80° C.) for more than 4 hours or overnight. The turbidity of zein in the plate was measured as A630 and the relative activity (higher/lower temperatures) was determined as an indicator of thermoactivity improvement. The clones with higher relative activity than the parental variant were selected and the sequence was determined.

Remaining Activity Assay

Yeast clones on SC-glucose were inoculated to a well of a 96-well micro titre plate and cultivated at 28° C. for 3 days. Protease activity was measured at 65° C. using azo-casein (Megazyme) after incubating the culture supernatant in 20 mM sodium acetate buffer, pH 4.5, for 10 min at a certain temperature (80° C. or 84° C. with 4° C. as a reference) to determine the remaining activity. The clones with higher remaining activity than the parental variant were selected and the sequence was determined.

Azo-Casein Assay 20 microL of samples were mixed with 150 microL of substrate solution (4 ml. of 12.5% azo-casein in ethanol in 96 ml. of 20 mM sodium acetate, pH 4.5, containing 0.01% triton-100 and 0.25 mM ZnSO4) and incubated for 4 hours or longer.

After adding 20 microL/well of 100% trichloroacetic acid (TCA) solution, the plate was centrifuged and 100 microL of supernatants were pipetted out to measure A440.

Expression of Protease Variants in *Aspergillus oryzae*

The constructs comprising the protease variant genes were used to construct expression vectors for *Aspergillus*. The *Aspergillus* expression vectors consist of an expression cassette based on the *Aspergillus niger* neutral amylase II promoter fused to the *Aspergillus nidulans* triose phosphate isomerase non-translated leader sequence (Pna2/tpi) and the *Aspergillus niger* amyloglycosidase terminator (Tamg). Also present on the plasmid was the *Aspergillus* selective marker amdS from *Aspergillus nidulans* enabling growth on acetamide as sole nitrogen source. The expression plasmids for protease variants were transformed into *Aspergillus* as described in Lassen et al., 2001, Appl. Environ. Microbiol. 67: 4701-4707. For each of the constructs 10-20 strains were isolated, purified and cultivated in shake flasks.

Purification of Expressed Variants

1. Adjust pH of the 0.22 µm filtered fermentation sample to 4.0.
2. Put the sample on an ice bath with magnetic stirring. Add (NH$_4$)$_2$SO$_4$ in small aliquots (corresponding to approx. 2.0-2.2 M (NH$_4$)$_2$SO$_4$ not taking the volume increase into account when adding the compound).
3. After the final addition of ((NH$_4$)$_2$SO$_4$, incubate the sample on the ice bath with gentle magnetic stirring for min. 45 min.
4. Centrifugation: Hitachi himac CR20G High-Speed Refrigerated Centrifuge equipped with R20A2 rotor head, 5° C., 20,000 rpm, 30 min.
5. Dissolve the formed precipitate in 200 mL 50 mM Na-acetate pH 4.0.
6. Filter the sample by vacuum suction using a 0.22 micro m PES PLUS membrane (IWAKI).
7. Desalt/buffer-exchange the sample to 50 mM Na-acetate pH 4.0 using ultrafiltration (Vivacell 250 from Vivascience equipped with 5 kDa MWCO PES membrane) overnight in a cold room. Dilute the retentate sample to 200 ml using 50 mM Na-acetate pH 4.0. The conductivity of sample is preferably less than 5 mS/cm.
8. Load the sample onto a cation-exchange column equilibrated with 50 mM Na-acetate pH 4.0. Wash unbound sample out of the column using 3 column volumes of binding buffer (50 mM Na-acetate pH 4.0), and elute the sample using a linear gradient, 0-100% elution buffer (50 mM Na-acetate+1 M NaCl pH 4.0) in 10 column volumes.
9. The collected fractions are assayed by an endo-protease assay (cf. below) followed by standard SDS-PAGE (reducing conditions) on selected fractions. Fractions are pooled based on the endo-protease assay and SDS-PAGE.

Endo-Protease Assay

1. Protazyme OL tablet/5 ml 250 mM Na-acetate pH 5.0 is dissolved by magnetic stirring (substrate: endo-protease Protazyme AK tablet from Megazyme—cat. #PRAK 1 1/08).
2. With stirring, 250 microL of substrate solution is transferred to a 1 0.5 mL Eppendorf tube.
3. 25 microL of sample is added to each tube (blank is sample buffer).
4. The tubes are incubated on a Thermomixer with shaking (1000 rpm) at 50° C. for 15 minutes.
5. 250 microL of 1 M NaOH is added to each tube, followed by vortexing.
6. Centrifugation for 3 min. at 16,100×G and 25° C.
7. 200 microL of the supernatant is transferred to a MTP, and the absorbance at 590 nm is recorded.

TABLE 1

Relative Activity of protease variants. Numbering of substitution(s) starts from N-terminal of the mature peptide in amino acids 1 to 177 of SEQ ID NO: 3.

| Variant | Substitution(s) and/or deletion(s) | Remaining Activity 80° C. | 84° C. |
|---|---|---|---|
| JTP082 | AS5/D79L/S87P/A112P/D142L | | 53% |
| JTP091 | D79L/S87P/A112P/T124V/D142L | 43% | |
| JTP092 | AS5/N26R/D79L/S87P/A112P/D142L | | 60% |
| JTP095 | N26R/T46R/D79L/S87P/A112P/D142L | | 62% |
| JTP096 | T46R/D79L/S87P/T116V/D142L | | 67% |
| JTP099 | D79L/P81R/S87P/A112P/D142L | | 80% |
| JTP101 | A27K/D79L/S87P/A112P/T124V/D142L | 81% | |
| JTP116 | D79L/Y82F/S87P/A112P/T124V/D142L | 59% | |
| JTP117 | D79L/Y82F/S87P/A112P/T124V/D142L | 94% | |
| JTP127 | D79L/S87P/A112P/T124V/A126V/D142L | 53% | |

TABLE 2

Relative Activity of protease variants. Numbering of substitution(s) starts from N-terminal of the mature peptide in amino acids 1 to 177 of SEQ ID NO: 3.

| Variant | Substitutions | Relative Activity 80° C./ 70° C. | 85° C./ 70° C. |
|---|---|---|---|
| JTP050 | D79L S87P A112P D142L | 23% | 9% |
| JTP134 | D79L Y82F S87P A112P D142L | 40% | |
| JTP135 | S38T D79L S87P A112P A126V D142L | 62% | |
| JTP136 | D79L Y82F S87P A112P A126V D142L | 59% | |
| JTP137 | A27K D79L S87P A112P A126V D142L | 54% | |
| JTP145 | S49P D79L S87P A112P D142L | 59% | |
| JTP146 | S50P D79L S87P A112P D142L | 63% | |
| JTP148 | D79L S87P D104P A112P D142L | 64% | |
| JTP161 | D79L Y82F S87G A112P D142L | 30% | 12% |
| JTP180 | S70V D79L Y82F S87G Y97W A112P D142L | 52% | |
| JTP181 | D79L Y82F S87G Y97W D104P A112P D142L | 45% | |
| JTP187 | S70V D79L Y82F S87G A112P D142L | 45% | |
| JTP188 | D79L Y82F S87G D104P A112P D142L | 43% | |
| JTP189 | D79L Y82F S87G A112P A126V D142L | 46% | |
| JTP193 | Y82F S87G S70V D79L D104P A112P D142L | | 15% |
| JTP194 | Y82F S87G D79L D104P A112P A126V D142L | | 22% |
| JTP196 | A27K D79L Y82F S87G D104P A112P A126V D142L | | 18% |

TABLE 3

Relative Activity of protease variants. Numbering of substitution(s) starts from N-terminal of the mature peptide in amino acids 1 to 177 of SEQ ID NO: 3.

| Variant | Substitutions | Relative Activity 80° C./70° C. |
|---|---|---|
| JTP196 | A27K D79L Y82F S87G D104P A112P A126V D142L | 55% |
| JTP210 | A27K Y82F S87G D104P A112P A126V D142L | 36% |
| JTP211 | A27K D79L Y82F D104P A112P A126V D142L | 44% |
| JTP213 | A27K Y82F D104P A112P A126V D142L | 37% |

Example 2

Temperature Profile of Selected Protease Variants Using Purified Enzymes

Selected protease variants showing good thermostability were purified and the purified enzymes were used in a zein-BCA assay as described below. The remaining protease activity was determined at 60° C. after incubation of the enzyme at elevated temperatures as indicated for 60 min.

Zein-BCA assay:

Zein-BCA assay was performed to detect soluble protein quantification released from zein by variant proteases at various temperatures.

Protocol:

1) Mix 10 microL of 10 micro g/mL enzyme solutions and 100 microL of 0.025% zein solution in a micro titer plate (MTP).

2) Incubate at various temperatures for 60 min.

3) Add 10 microL of 100% trichloroacetic acid (TCA) solution.

4) Centrifuge MTP at 3500 rpm for 5 min.

5) Take out 15 microL to a new MTP containing 100 microL of BCA assay solution (Pierce Cat #:23225, BCA Protein Assay Kit).

6) Incubate for 30 min. at 60° C.

7) Measure A562.

The results are shown in Table 4. All of the tested protease variants showed an improved thermostability as compared to the wild type (WT) protease.

Example 3

Determination of Relative Activity for Proteases Using Azo Casein Assay 20 microL of samples containing approx. 0.01 mg/ml were mixed with 150 microL of substrate solution (4 mL of 12. 5% azo-casein in ethanol in 96 m of 20 mM sodium acetate, pH 4. 5, containing 0. 01% triton-100 and 0. 25 mM ZnSO4) and incubated for 5 hours at 70° C. and 80° C.

After adding 20 microL/well of 100% trichloroacetic acid (TCA) solution, the plate was centrifuged and 80 microL of supernatants were pipetted out to measure A440.

| Sample name | Relative Activity 80° C./70° C. |
|---|---|
| Protease RH | 34% |
| Protease TF | 106% |
| Portease OX | 19% |
| Protease PF | 154% |

Example 4

Extracting Oil using Protease and Phospholipase

The purpose of this experiment was to extract oil using a combination og MG Prot 3 and Phospholipase PL99.

Method

Fermentation: Industrially mash liquefied with Avantec™ (alpha-amylase product available from Novozymes) was stored frozen. Two liters of mash were thawed for approximately 2 hours prior to starting this study. The dry solids (DS) content of the mash was measured on a Mettler-Toledo moisture balance, with a resulting value of 32.88% DS. The mash was prepared to 500 ppm urea and 3 ppm penicillin using solutions of 200 g/L urea and 1 g/L penicillin, respectively, and adjusted to pH 5 using 40% v/v $H_2SO_4$. Approximately 25 g of prepared mash was pipetted into 48 pre-weighed 50 mL centrifuge tubes, which had holes drilled in the top.

Red Star™ yeast was rehydrated, with 2.75 g of yeast placed in 50 mL of 32° C. tap water for 30 minutes. While the yeast soaked, each mash sample was dosed with diluted Spirizyme Achieve™ (glucoamylase product available from Novozymes) (0.076 AGU/μL) to an enzyme concentration of 0.600 AGU/g DS, as calculated by the following equation

TABLE 4

Zein-BCA assay

| WT/Variant | Sample incubated 60 min at indicated temperatures (° C.) (micro g/mL Bovine serum albumin equivalent peptide released) | | | | | | |
|---|---|---|---|---|---|---|---|
| | 60° C. | 70° C. | 75° C. | 80° C. | 85° C. | 90° C. | 95° C. |
| WT | 94 | 103 | 107 | 93 | 58 | 38 | |
| JTP050 (D79L + S87P + A112P + D142L) | 86 | 101 | 107 | 107 | 104 | 63 | 36 |
| JTP077 (A27K + D79L + S87P + A112P + D142L) | 82 | 94 | 104 | 105 | 99 | 56 | 31 |
| JTP188 (D79L + Y82F + S87G + D104P + A112P + D142L) | 71 | 83 | 86 | 93 | 100 | 75 | 53 |
| JTP196 (A27K + D79L + Y82F + S87G + D104P + A112P + D126V + D142L) | 87 | 99 | 103 | 106 | 117 | 90 | 38 |

$$Enz.\text{dose}(ml) = \frac{\text{Final } enz.\text{dose}(mg\ EP/g\ DS) \times}{\text{Slurry weight}(g) \times \text{Solid content}(\%\ DS)}{\text{Conc. enzyme}(mg\ EP/ml)}$$

The set of 48 tubes consisted of the following 16 treatments. In summary, there were only 2 treatments repeated multiple times to yield high oil quantity.

The protease used was the protease MG Prot 3, a protease having the amino acid sequence set out in SEQ ID NO: 14 herein. The phospholipase used (PL99) is derived from *Kionochaeta*. The amino acid sequence of the phospholipase PL99 is set out in SEQ ID NO: 15 herein.

TABLE 9

Treatments Tested

| Tube | Spirizyme ™ Achieve | Protease | Protease Dose | Phospholipase | Phospholipase Dose |
|---|---|---|---|---|---|
| 1 | 0.6 AGU/gDS | MG Prot 3 | 5 µg/gDS | | |
| 2 | 0.6 AGU/gDS | MG Prot 3 | 5 µg/gDS | | |
| 3 | 0.6 AGU/gDS | MG Prot 3 | 5 µg/gDS | | |
| 4 | 0.6 AGU/gDS | MG Prot 3 | 5 µg/gDS | | |
| 5 | 0.6 AGU/gDS | MG Prot 3 | 5 µg/gDS | | |
| 6 | 0.6 AGU/gDS | MG Prot 3 | 5 µg/gDS | | |
| 7 | 0.6 AGU/gDS | MG Prot 3 | 5 µg/gDS | | |
| 8 | 0.6 AGU/gDS | MG Prot 3 | 5 µg/gDS | | |
| 9 | 0.6 AGU/gDS | MG Prot 3 | 5 µg/gDS | PL99 | 5 µg/gDS |
| 10 | 0.6 AGU/gDS | MG Prot 3 | 5 µg/gDS | PL99 | 5 µg/gDS |
| 11 | 0.6 AGU/gDS | MG Prot 3 | 5 µg/gDS | PL99 | 5 µg/gDS |
| 12 | 0.6 AGU/gDS | MG Prot 3 | 5 µg/gDS | PL99 | 5 µg/gDS |
| 13 | 0.6 AGU/gDS | MG Prot 3 | 5 µg/gDS | PL99 | 5 µg/gDS |
| 14 | 0.6 AGU/gDS | MG Prot 3 | 5 µg/gDS | PL99 | 5 µg/gDS |
| 15 | 0.6 AGU/gDS | MG Prot 3 | 5 µg/gDS | PL99 | 5 µg/gDS |
| 16 | 0.6 AGU/gDS | MG Prot 3 | 5 µg/gDS | PL99 | 5 µg/gDS |

Water was dosed into each sample such that the total added volume of enzyme and water was 195 µL/25 g sample. All samples were dosed with 250 µL of rehydrated yeast solution and vortexed. Each sample was weighed when all samples had been dosed. The samples were placed in a shaking water bath set at 32° C. for 70 hours. Each sample was weighed after 70 hours of fermentation.

Distillation: A Büchi Multivapor evaporation system was used for all distillations. The unit distilled 24 samples at a time. The parameters used are shown in the following table. Tubes were weighed after distillation and weight lost during distillation was replaced with DI water. Tubes were weighed again after water addition.

| Time | 80 min |
|---|---|
| Temperature | 75° C. |
| Vacuum | 200-153 mBar (40 min) |
| | 153-148 mBar (40 min) |
| RPM | 8 |

Oil Extraction: Hexane was added to each sample at a dose of 0.125 mL hexane/1 g starting material. Each tube was covered in Dura-seal to prevent sample leakage, and mixed thoroughly. Tubes were centrifuged at 3,000×g for 10 minutes in an Avanti JE Series centrifuge with JS-5.3 rotor. After centrifugation, the oil/hexane layer (supernatant) was removed using a positive displacement pipette, transferred to a 50 ml volumetric flask. Tubes labelled 1-24 were added to the same flask (A) and tubes labelled 25-48 were added together in a second flask (B). After all the oil/hexane layers were extracted off, each treatment (+/−PL) was run on a Büchi Multivapor for about 5 minutes to evaporate the majority of the hexane layer off. The two oil samples were then poured into 50 ml tubes and left over the weekend for the rest of the hexane to evaporate off before testing.

| | Tube (A) (without PL) | Tube (B) (with PL) |
|---|---|---|
| Moisture (%) | 2.03 | 1.53 |
| Insolubles (%) | 0.14 | n.d. |
| Free fatty acid (%) | 8.92 | 9.59 |

Example 5

Extracting Oil using Protease and Phospholipase

The purpose of this experiment is to extract oil using a combination of a protease (Protease OX) and three different phospholipases (PL99, PL100 and PL101).

Method

Fermentation: Industrially mash liquefied with Avantec™ (alpha-amylase product available from Novozymes) was stored frozen. One liter of mash was thawed for approximately 2 hours prior to starting this study. The dry solids content of the mash was measured on a Mettler-Toledo moisture balance, with a resulting value of 32.17% DS. The mash was prepared to 500 ppm urea and 3 mg/L penicillin using solutions of 200 g/L urea and 1 g/L penicillin, respectively, and adjusted to pH 5 using 40% v/v H2SO4. Approximately 35 g of each prepared mash was pipetted into each of 24 pre-weighed 50 mL centrifuge tubes, which had holes drilled in the top.

The protease used was the Protease OX, a protease derived from *Thermoascus aurantiacus* having the amino acid sequence set out in SEQ ID NO: 3 herein. Three phospholipases were used (PL99, PL100 and PL101). Phospholipase PL99 is from *Kionochaeata* sp. and has the amino acid sequence as set out herein as SEQ ID NO: 15. Phospholipase PL100 is from *Penicillium emersonii* and has the amino acid sequence as set out herein as SEQ ID NO: 16. Phospholipase PL101 is from *Bacillus thuringensis* and has the amino acid sequence as set out herein as SEQ ID NO: 17.

Red Star™ yeast was rehydrated, with 2.75 g of yeast placed in 50 mL of 32° C. tap water for 30 minutes.

TABLE

Treatments tested

| Treatment | Protease | Protease Dose (µg/gDS) | PL | Units (ug/gDS) | Spirizyme Excel XHS (AGU/gDS) |
|---|---|---|---|---|---|
| 1 | None | 0 | none | 0 | 0.6 |
| 2 | None | 0 | PL99 | 100 | 0.6 |
| 3 | None | 0 | PL100 | 100 | 0.6 |
| 4 | None | 0 | PL101 | 100 | 0.6 |
| 5 | Protease OX | 5 | none | 0 | 0.6 |
| 6 | Protease OX | 5 | PL99 | 100 | 0.6 |
| 7 | Protease OX | 5 | PL100 | 100 | 0.6 |
| 8 | Protease OX | 5 | PL101 | 100 | 0.6 |

TABLE

Enzymes

| Name | Stock conc. | Units | Dilution factor | Experiment conc. | Units |
|---|---|---|---|---|---|
| Spirizyme Excel ™ XHS | 1234.2 | AGU/g | 12.40 | 99.56 | AGU/g |
| Protease OX (Batch 10) | 25.25 | mg/g | 24.79 | 1.02 | µg/µl |
| PL99 | 5.5 | mg/ml | 1.00 | 5.50 | µg/µl |
| PL100 | 24 | mg/ml | 1.00 | 24.00 | µg/µl |
| PL101 | 2 | mg/ml | 1.00 | 2.00 | µg/µl |

Enzyme doses were calculated via the following equation:

$$Enz.\text{dose}(ml) = \frac{\text{Final } enz.\text{dose}(AGU/g\ DS) \times \text{Mash weight}(g) \times \text{Solid content}(\%\ DS)}{\text{Conc. enzyme}(mg\ AGU/ml)}$$

TABLE 12

Enzyme Dosing

| Treatment (protease, phospholipase) (dose µg/g DS) | Sample # | Spirizyme Excel (µL) | Protease (µL) | PL(µL) | H₂O (µL) | Total to add (µL) | Yeast (µL) |
|---|---|---|---|---|---|---|---|
| 1 None, 0.0 | 1 | 70.9 | 0.0 | 0.0 | 639.9 | 256.06 | 350 |
| 1 | 2 | 70.0 | 0.0 | 0.0 | 627.6 | 252.88 | 350 |
| 1 | 3 | 69.6 | 0.0 | 0.0 | 622.0 | 251.43 | 350 |
| 2 None, PL99 100 | 4 | 70.7 | 0.0 | 213.4 | 423.8 | 255.34 | 350 |
| 2 | 5 | 70.9 | 0.0 | 213.9 | 425.7 | 255.99 | 350 |
| 2 | 6 | 70.9 | 0.0 | 213.9 | 425.7 | 255.99 | 350 |
| 3 None, PL100 100 | 7 | 71.2 | 0.0 | 49.2 | 595.0 | 257.19 | 350 |
| 3 | 8 | 71.2 | 0.0 | 49.2 | 594.7 | 257.12 | 350 |
| 3 | 9 | 70.9 | 0.0 | 49.0 | 590.0 | 255.82 | 350 |
| 4 None, PL101 100 | 10 | 71.2 | 0.0 | 590.3 | 52.8 | 256.89 | 350 |
| 4 | 11 | 71.2 | 0.0 | 590.8 | 53.2 | 257.11 | 350 |
| 4 | 12 | 69.8 | 0.0 | 579.0 | 45.1 | 251.99 | 350 |
| 5 Protease OX, 5.0 | 13 | 69.9 | 57.0 | 0.0 | 605.0 | 251.47 | 350 |
| 5 | 14 | 70.4 | 57.3 | 0.0 | 611.4 | 256.81 | 350 |
| 5 | 15 | 68.3 | 55.6 | 0.0 | 582.6 | 249.60 | 350 |
| 6 Protease OX, | 16 | 69.7 | 56.7 | 210.1 | 391.2 | 255.79 | 350 |
| 6 PL99 100 | 17 | 71.1 | 57.9 | 214.6 | 407.0 | 254.25 | 350 |
| 6 | 18 | 69.1 | 56.3 | 208.6 | 385.7 | 253.11 | 350 |
| 7 Protease OX, | 19 | 70.8 | 57.7 | 49.0 | 568.7 | 253.31 | 350 |
| 7 PL100 100 | 20 | 70.4 | 57.4 | 48.7 | 563.2 | 253.55 | 350 |
| 7 | 21 | 70.1 | 57.1 | 48.5 | 559.1 | 253.95 | 350 |
| 8 Protease OX, | 22 | 70.2 | 57.2 | 582.1 | 26.2 | 0.00 | 350 |
| 8 PL101 100 | 23 | 70.2 | 57.2 | 582.6 | 26.6 | 0.00 | 350 |
| 8 | 24 | 70.3 | 57.3 | 583.5 | 27.2 | 0.00 | 350 |

Water was dosed into each sample such that the total added volume of enzyme and water was 725 and 750 µL/35 g sample. All samples were dosed with 350 µL of rehydrated yeast solution and vortexed. Each sample was weighed when all samples had been dosed. The samples were placed in a shaking incubator set at 32° C. for 70 hours. Each sample was weighed after 70 hours of fermentation to monitor ethanol production.

Distillation: A Büchi Multivapor evaporation system was used for all distillations. The unit distilled 12 samples at a time. The parameters used are shown in the table below. Tubes were weighed after distillation and weight lost during distillation was replaced with DI water. Tubes were weighed again after water addition.

| | |
|---|---|
| Time | 80 min |
| Temperature | 75 ° C. |
| Vacuum | 200-153 mBar (40 min) |
| | 153-148 mBar (40 min) |
| RPM | 8 |

Oil Extraction: Hexane was added to each sample at a dose of 0.125 mL hexane/1 g starting material. Each tube was covered in Dura-seal to prevent sample leakage, and mixed thoroughly. Tubes were centrifuged at 3,000×g for 10 minutes in an Avanti JE Series centrifuge with JS-5.3 rotor. After centrifugation, the oil/hexane layer (supernatant) was removed using a positive displacement pipette, transferred to 15 mL screw-cap tubes. Tubes were allowed stand open in a chemical hood so that the hexane would be evaporated. Tubes were filmed, capped, and tested.

| Protease | PLC | | HPLC DG % | ICP P (ppm) | NMR P (ppm) |
|---|---|---|---|---|---|
| None | None | Sample 1 | 1.7 | 52 | 52 |
| None | PL99 | Sample 2 | 6.2 | 35 | 52 |
| None | PL100 | Sample 3 | 2.8 | 28 | 34 |
| None | PL101 | Sample 4 | 3.3 | 31 | 41 |
| Protease OX | None | Sample 5 | 2.1 | 20 | 43 |
| Protease OX | PL99 | Sample 6 | 6.4 | 48 | 36 |
| Protease OX | PL100 | Sample 7 | 3.2 | 38 | 0 |
| Protease OX | PL101 | Sample 8 | 3.6 | 35 | 57 |

Conclusion

Percent diglyceride (DG) increased with the use of phospholipase-C, with phospholipase PL99 performing the best.

Example 6

The purpose of this experiment is to extract oil using Protease OX alone and a Protease OX in combination with three different doses of a phospholipase (PL99) so that it may be evaluated for oil quality (degumming).

Method

Fermentation: Industrially mash liquefied with Avantec™ (alpha-amylase product available from Novozymes) was stored frozen. One liter of mash was thawed for approximately 2 hours prior to starting this study. The dry solids content of the mash was measured on a Mettler-Toledo moisture balance, with a resulting value of 32.04% DS. The mash was prepared to 500 ppm urea and 3 mg/L penicillin using solutions of 200 g/L urea and 1 g/L penicillin, respectively, and adjusted to pH 5 using 40% v/v $H_2SO_4$. Approximately 35 g of each prepared mash was pipetted into each of 24 pre-weighed 50 mL centrifuge tubes, which had holes drilled in the top.

The protease used was the Protease OX, a thermostable protease derived from *Thermoascus aurantiacus* having the amino acid sequence set out in SEQ ID NO: 3 herein. Phospholipase PL99 is from *Kionochaeata* sp. and has the amino acid sequence as set out herein as SEQ ID NO: 15.

Red Star™ yeast was rehydrated, with 2.75 g of yeast placed in 50 mL of 32° C. tap water for 30 minutes. While the yeast soaked, each mash sample was dosed with diluted Spirizyme Excel™ XHS (glucoamylase product available from Novozymes) (0.07 AGU/µL) to an enzyme concentration of 0.600 AGU/g DS, as calculated by the following equation.

$$Enz.\text{dose}(ml) = \frac{\text{Final } enz.\text{dose}(AGU/g\ DS) \times \text{Mash weight}(g) \times \text{Solid content}(\%\ DS)}{Conc.\ \text{enzyme}(mg\ AGU/ml)}$$

Each set of 6 tubes consisted of the following 4 treatments:

TABLE

Treatments tested

| Treatment | Protease | Dose | Units | PL | Dose | Units | GA | Dose | Units |
|---|---|---|---|---|---|---|---|---|---|
| 1 | Protease OX | 5 | µg/gDS | none | 0.000 | µg/gDS | Sp. Excel | 0.6 | AGU/gDS |
| 2 | Protease OX | 5 | µg/gDS | PL99 | 1 | µg/gDS | Sp. Excel | 0.6 | AGU/gDS |
| 3 | Protease OX | 5 | µg/gDS | PL99 | 5 | µg/gDS | Sp. Excel | 0.6 | AGU/gDS |
| 4 | Protease OX | 5 | µg/gDS | PL99 | 100 | µg/gDS | Sp. Excel | 0.6 | AGU/gDS |

Water was dosed into each sample such that the total added volume of enzyme and water was 400 µL/25 g sample. All samples were dosed with 350 µL of rehydrated yeast solution and vortexed. Each sample was weighed when all samples had been dosed. The samples were placed in a shaking incubator set at 32° C. for 70 hours. Each sample was weighed after 70 hours of fermentation to monitor ethanol production.

Distillation: A Büchi Multivapor evaporation system was used for all distillations. The unit distilled 24 samples at a time. The parameters are shown in the following table. Tubes were weighed after distillation and weight lost during distillation was replaced with DI water. Tubes were weighed again after water addition.

| Time | 80 min |
|---|---|
| Temperature | 75 ° C. |
| Vacuum | 200-153 mBar (40 min) |
| | 153-148 mBar (40 min) |
| RPM | 8 |

Oil Extraction: Hexane was added to each sample at a dose of 0.125 mL hexane/1 g starting material. Each tube was covered in Dura-seal to prevent sample leakage, and mixed thoroughly. Tubes were centrifuged at 3,000×g for 10 minutes in an Avanti JE Series centrifuge with JS-5.3 rotor. After centrifugation, the oil/hexane layer (supernatant) was removed using a positive displacement pipette, transferred to a 5 mL vial. Vials were wrapped, sealed, and tested.

| Sample ID | 1.3 DG (DG % content) | 1.2 DG (DG % content) | Total DG (DG % content) |
|---|---|---|---|
| 1 | 1.67 | 0.73 | 2.39 |
| 2 | 1.69 | 0.77 | 2.47 |
| 3 | 1.67 | 0.72 | 2.39 |
| 4 | 1.69 | 0.76 | 2.45 |
| 5 | 1.70 | 0.76 | 2.46 |
| 6 | 1.75 | 0.77 | 2.51 |
| 7 | 2.10 | 1.24 | 3.33 |
| 8 | 2.07 | 1.22 | 3.29 |
| 9 | 2.03 | 1.19 | 3.22 |
| 10 | 2.07 | 1.23 | 3.29 |
| 11 | 2.04 | 1.21 | 3.25 |
| 12 | 2.06 | 1.24 | 3.30 |
| 13 | 2.28 | 1.51 | 3.78 |
| 14 | 2.22 | 1.49 | 3.72 |
| 15 | 2.23 | 1.48 | 3.71 |
| 16 | 2.28 | 1.52 | 3.80 |
| 17 | 2.21 | 1.48 | 3.69 |
| 18 | 2.28 | 1.50 | 3.79 |
| 19 | 3.25 | 2.82 | 6.08 |
| 20 | 3.31 | 2.80 | 6.10 |
| 21 | 3.32 | 2.82 | 6.14 |
| 22 | 3.29 | 2.82 | 6.11 |

-continued

| Sample ID | 1.3 DG (DG % content) | 1.2 DG (DG % content) | Total DG (DG % content) |
|---|---|---|---|
| 23 | 3.34 | 2.90 | 6.24 |
| 24 | 3.43 | 3.00 | 6.43 |

Conclusions: Treatments 2 and 3 (5 µg Protease OX with 1 and 5 µg of PLC, respectively) yielded similar results in % diglyceride (DG) content. 1.3 DG refers to a diglyceride with fatty acid moieties on the first and third carbons of the glycerol backbone. 1.2 DG refers to a diglyceride with fatty acid moieties on the first and second carbons of the glycerol backbone. The diglycerides are formed by the hydrolysis of a phospholipid by a phospholipase. Treatment 4 (5 µg Protease OX with 100 µg of PLC) nearly doubled the % DG.

The invention claimed is:

1. A process of recovering oil, comprising
(a) converting a starch-containing material into dextrins with an alpha-amylase;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease and a phospholipase are present and/or added during steps (a) to (c);
wherein the protease present and/or added in steps (a) to (c) is a protease having the amino acid sequence set out in SEQ ID NO: 10 or a protease having at least 60% identity to SEQ ID NO: 10 and having protease activity; and
wherein the phospholipase present and/or added in steps (a) to (c) is:
(i) the phospholipase shown in SEQ ID NO: 15 or one having a sequence identity thereto of at least 90% and having phospholipase activity;
(ii) the phospholipase shown in SEQ ID NO: 16 or one having a sequence identity thereto of at least 90% and having phospholipase activity; or
(iii) the phospholipase shown in SEQ ID NO: 17 or one having a sequence identity thereto of at least 90% and having phospholipase activity.

2. The process of claim 1, wherein the protease and the phospholipase are present and/or added during steps (b) and/or (c).

3. The process of claim 1, wherein the protease is added together with the alpha-amylase in step (a).

4. The process of claim 1, wherein the phospholipase present and/or added in steps (a) to (c) is the phospholipase shown in SEQ ID NO: 15 or one having a sequence identity thereto of at least 90% and having phospholipase activity.

5. The process of claim 1, wherein the phospholipase present and/or added in steps (a) to (c) is the phospholipase shown in SEQ ID NO: 15 or one having a sequence identity thereto of at least 95% and having phospholipase activity.

6. The process of claim 1, wherein the phospholipase present and/or added in steps (a) to (c) is the phospholipase shown in SEQ ID NO: 16 or one having a sequence identity thereto of at least 90% having phospholipase activity.

7. The process of claim 1, wherein the phospholipase present and/or added in steps (a) to (c) is the phospholipase shown in SEQ ID NO: 16 or one having a sequence identity thereto of at least 95% having phospholipase activity.

8. The process of claim 1, wherein the phospholipase present and/or added in steps (a) to (c) is the phospholipase shown in SEQ ID NO: 17 or one having a sequence identity thereto of at least 90% and having phospholipase activity.

9. The process of claim 1, wherein the phospholipase present and/or added in steps (a) to (c) is the phospholipase shown in SEQ ID NO: 17 or one having a sequence identity thereto of at least 95% and having phospholipase activity.

10. The process of claim 1, wherein the protease and the phospholipase are added sequentially.

11. The process of claim 1, wherein the protease and the phospholipase are added simultaneously.

12. The process of claim 1, wherein the step (a) is performed at a temperature above the initial gelatinization temperature.

13. The process of claim 1, wherein a protease is added in step (a) carried out above the initial gelatinization temperature.

14. The process of claim 1, wherein the step (a) is performed a temperature below the initial gelatinization temperature.

15. The process of claim 1, wherein saccharification step (b) and fermentation step (c) are carried out simultaneously.

16. The process of claim 1, wherein saccharification step (b) and fermentation step (c) are carried out sequentially.

17. The process of claim 1, wherein steps (a), (b) and (c) are carried out simultaneously at a temperature below the initial gelatinization temperature.

18. The process of claim 1, wherein steps (a), (b) and (c) are carried out sequentially at a temperature below the initial gelatinization temperature.

19. A process of recovering oil, comprising
(a) converting a starch-containing material into dextrins with an alpha-amylase;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease and a phospholipase are present and/or added during steps (a) to (c);
wherein the protease present and/or added in steps (a) to (c) is a protease having the amino acid sequence set out in SEQ ID NO: 4 or a protease having at least 70% identity to SEQ ID NO: 4 and having protease activity; and wherein the phospholipase present and/or added in steps (a) to (c) is:

(i) the phospholipase shown in SEQ ID NO: 15 or one having a sequence identity thereto of at least 90% and having phospholipase activity;

(ii) the phospholipase shown in SEQ ID NO: 16 or one having a sequence identity thereto of at least 90% and having phospholipase activity; or (iii) the phospholipase shown in SEQ ID NO: 17 or one having a sequence identity thereto of at least 90% and having phospholipase activity.

20. The process of claim 19, wherein the protease and the phospholipase are present and/or added during steps (b) and/or (c).

21. The process of claim 19, wherein the protease is added together with the alpha-amylase in step (a).

22. The process of claim 19, wherein the phospholipase present and/or added in steps (a) to (c) is the phospholipase shown in SEQ ID NO: 15 or one having a sequence identity thereto of at least 90% and having phospholipase activity.

23. The process of claim 19, wherein the phospholipase present and/or added in steps (a) to (c) is the phospholipase shown in SEQ ID NO: 15 or one having a sequence identity thereto of at least 95% and having phospholipase activity.

24. The process of claim 19, wherein the phospholipase present and/or added in steps (a) to (c) is the phospholipase shown in SEQ ID NO: 16 or one having a sequence identity thereto of at least 90% having phospholipase activity.

25. The process of claim 19, wherein the phospholipase present and/or added in steps (a) to (c) is the phospholipase shown in SEQ ID NO: 16 or one having a sequence identity thereto of at least 95% having phospholipase activity.

26. The process of claim 19, wherein the phospholipase present and/or added in steps (a) to (c) is the phospholipase shown in SEQ ID NO: 17 or one having a sequence identity thereto of at least 90% and having phospholipase activity.

27. The process of claim 19, wherein the phospholipase present and/or added in steps (a) to (c) is the phospholipase shown in SEQ ID NO: 17 or one having a sequence identity thereto of at least 95% and having phospholipase activity.

28. The process of claim 19, wherein the protease and the phospholipase are added sequentially.

29. The process of claim 19, wherein the protease and the phospholipase are added simultaneously.

30. The process of claim 19, wherein the step (a) is performed at a temperature above the initial gelatinization temperature.

31. The process of claim 19, wherein a protease is added in step (a) carried out above the initial gelatinization temperature.

32. The process of claim 19, wherein the step (a) is performed a temperature below the initial gelatinization temperature.

33. The process of claim 19, wherein saccharification step (b) and fermentation step (c) are carried out simultaneously.

34. The process of claim 19, wherein saccharification step (b) and fermentation step (c) are carried out sequentially.

35. The process of claim 19, wherein steps (a), (b) and (c) are carried out simultaneously at a temperature below the initial gelatinization temperature.

36. The process of claim 19, wherein steps (a), (b) and (c) are carried out sequentially at a temperature below the initial gelatinization temperature.

37. The process of claim 19, wherein the protease present and/or added in steps (a) to (c) is a protease having the amino acid sequence set out in SEQ ID NO: 4 or a protease having at least 75% identity to SEQ ID NO: 4 and having protease activity.

38. The process of claim 19, wherein the protease present and/or added in steps (a) to (c) is a protease having the amino acid sequence set out in SEQ ID NO: 4 or a protease having at least 80% identity to SEQ ID NO: 4 and having protease activity.

39. The process of claim 19, wherein the protease present and/or added in steps (a) to (c) is a protease having the amino acid sequence set out in SEQ ID NO: 4 or a protease having at least 85% identity to SEQ ID NO: 4 and having protease activity.

40. The process of claim 19, wherein the protease present and/or added in steps (a) to (c) is a protease having the amino acid sequence set out in SEQ ID NO: 4 or a protease having at least 85% identity to SEQ ID NO: 4 and having protease activity.

41. The process of claim 19, wherein the protease present and/or added in steps (a) to (c) is a protease having the amino acid sequence set out in SEQ ID NO: 4 or a protease having at least 90% identity to SEQ ID NO: 4 and having protease activity.

42. The process of claim 19, wherein the protease present and/or added in steps (a) to (c) is a protease having the amino acid sequence set out in SEQ ID NO: 4 or a protease having at least 90% identity to SEQ ID NO: 4 and having protease activity.

43. The process of claim 19, wherein the protease present and/or added in steps (a) to (c) is a protease having the amino acid sequence set out in SEQ ID NO: 4 or a protease having at least 95% identity to SEQ ID NO: 4 and having protease activity.

* * * * *